US010610384B2

(12) United States Patent
Byars et al.

(10) Patent No.: US 10,610,384 B2
(45) Date of Patent: Apr. 7, 2020

(54) LOWER LIMB PROSTHESIS

(71) Applicant: Freedom Innovations, LLC, Irvine, CA (US)

(72) Inventors: Jonathan M. Byars, Orange, CA (US); Hugo Quintero, Santa Ana, CA (US); John Carpenter, Santa Ana, CA (US)

(73) Assignee: Freedom Innovations, LLC, Irvine, CA (US)

( * ) Notice: Subject to any disclaimer, the term of this patent is extended or adjusted under 35 U.S.C. 154(b) by 104 days.

(21) Appl. No.: 15/694,404

(22) Filed: Sep. 1, 2017

(65) Prior Publication Data

US 2018/0116826 A1   May 3, 2018

Related U.S. Application Data

(63) Continuation of application No. PCT/US2016/021074, filed on Mar. 4, 2016.

(60) Provisional application No. 62/128,371, filed on Mar. 4, 2015.

(51) Int. Cl.
| | |
|---|---|
| *A61F 2/66* | (2006.01) |
| *A61F 2/70* | (2006.01) |
| *A61F 2/68* | (2006.01) |
| *A61F 2/50* | (2006.01) |

(52) U.S. Cl.
CPC .............. *A61F 2/6607* (2013.01); *A61F 2/66* (2013.01); *A61F 2/68* (2013.01); *A61F 2/70* (2013.01); *A61F 2002/5073* (2013.01); *A61F 2002/5075* (2013.01); *A61F 2002/6614* (2013.01); *A61F 2002/6836* (2013.01); *A61F 2002/704* (2013.01)

(58) Field of Classification Search
CPC .. A61F 2/66; A61F 2/6607; A61F 2002/5072; A61F 2002/5073; A61F 2002/5075; A61F 2002/5076; A61F 2002/5078; A61F 2002/5079; A61F 2002/6614; A61F 2002/6621; A61F 2002/6628; A61F 2002/6635; A61F 2002/6642; A61F 2002/665; A61F 2002/6657; A61F 2002/6664; A61F 2002/6671; A61F 2002/6678; A61F 2002/6685; A61F 2002/6692

See application file for complete search history.

(56) References Cited

U.S. PATENT DOCUMENTS

| | | | |
|---|---|---|---|
| 4,209,860 | A | 7/1980 | Graupe |
| 4,382,311 | A | 5/1983 | Watts |
| 4,685,925 | A | 8/1987 | Childress et al. |
| 4,707,882 | A | 11/1987 | Watts |
| 4,777,765 | A | 10/1988 | Johnson, Jr. |

(Continued)

FOREIGN PATENT DOCUMENTS

| | | |
|---|---|---|
| EP | 2 770 956 B1 | 12/2017 |
| WO | WO-2010/027968 A2 | 3/2010 |

(Continued)

OTHER PUBLICATIONS

Au et al., An EMG-Position controlled system for an active ankle-foot prosthesis: an initial experimental study, 2005.

(Continued)

*Primary Examiner* — Christie L Bahena
(74) *Attorney, Agent, or Firm* — Dorsey & Whitney LLP

(57) ABSTRACT

Powered limb prostheses with multi-stage transmissions are provided.

13 Claims, 21 Drawing Sheets

(56) References Cited

U.S. PATENT DOCUMENTS

| | | | |
|---|---|---|---|
| 4,787,174 | A | 11/1988 | Brown |
| 4,883,493 | A | 11/1989 | Martel et al. |
| 5,043,929 | A | 8/1991 | Kramer et al. |
| 5,246,465 | A | 9/1993 | Rincoe et al. |
| 5,459,963 | A | 10/1995 | Alexander |
| 5,893,891 | A | 4/1999 | Zahedi |
| 5,927,011 | A | 7/1999 | Sickenius |
| 5,954,678 | A * | 9/1999 | Cruz ................... A61F 5/0125 602/16 |
| 6,112,461 | A | 9/2000 | Cheng |
| 6,412,220 | B1 | 7/2002 | Lindley |
| 6,470,948 | B2 | 10/2002 | Yates et al. |
| 6,706,074 | B1 * | 3/2004 | Chen ................... A61F 2/644 623/44 |
| 6,711,857 | B1 | 3/2004 | Wagnitz et al. |
| 7,153,242 | B2 | 12/2006 | Goffer |
| 7,429,253 | B2 | 9/2008 | Shimada et al. |
| 7,628,766 | B1 | 12/2009 | Kazerooni et al. |
| 7,799,091 | B2 | 9/2010 | Herr et al. |
| 8,057,550 | B2 | 11/2011 | Clausen et al. |
| 8,736,087 | B2 | 5/2014 | Mullins et al. |
| 8,828,093 | B1 | 9/2014 | Kuiken et al. |
| 9,180,025 | B2 | 11/2015 | Goldfarb et al. |
| 2004/0039454 | A1 | 2/2004 | Herr et al. |
| 2004/0049290 | A1 | 3/2004 | Bedard |
| 2004/0054423 | A1 | 3/2004 | Martin |
| 2004/0064195 | A1 | 4/2004 | Herr |
| 2004/0088057 | A1 | 5/2004 | Bedard |
| 2004/0111163 | A1 | 6/2004 | Bedard et al. |
| 2005/0113973 | A1 | 5/2005 | Endo et al. |
| 2006/0173552 | A1 | 8/2006 | Roy |
| 2006/0184280 | A1 | 8/2006 | Oddsson et al. |
| 2006/0224247 | A1 | 10/2006 | Clausen et al. |
| 2006/0249315 | A1 | 11/2006 | Herr et al. |
| 2007/0043449 | A1 | 2/2007 | Herr et al. |
| 2007/0050044 | A1 | 3/2007 | Haynes et al. |
| 2007/0123997 | A1 | 5/2007 | Herr et al. |
| 2009/0192619 | A1 | 7/2009 | Martin et al. |
| 2009/0265018 | A1 | 10/2009 | Goldfarb et al. |
| 2009/0299489 | A1 | 12/2009 | Gramnaes |
| 2009/0326677 | A1 | 12/2009 | Phillips et al. |
| 2010/0094431 | A1 | 4/2010 | Albrecht-Laatsch et al. |
| 2010/0114329 | A1 | 5/2010 | Casler et al. |
| 2011/0112447 | A1 | 5/2011 | Hsiao-Wecksler et al. |
| 2011/0166674 | A1 | 7/2011 | Montmartin |
| 2011/0213599 | A1 | 9/2011 | Jacobsen et al. |
| 2011/0224803 | A1 | 9/2011 | Goldfarb et al. |
| 2011/0257764 | A1 | 10/2011 | Herr et al. |
| 2012/0259431 | A1 | 10/2012 | Han et al. |
| 2012/0330439 | A1 | 12/2012 | Goldfarb et al. |

FOREIGN PATENT DOCUMENTS

| | | |
|---|---|---|
| WO | WO-2010/027968 A3 | 3/2010 |
| WO | WO-2011/026086 A1 | 3/2011 |
| WO | WO-2011/096965 A9 | 8/2011 |

OTHER PUBLICATIONS

Au et al., An ankle-foot emulation system for the study of human walking biomechanics, 2006.

Au et al., Powered ankle-foot prosthesis to assist level-ground and stair-descent gaits, 2008.

Au et al., Biomechanical design of a powered ankle-foot prosthesis, 2007.

Bellman et al., SPARKy3: Design of an active robotic ankle prosthesis with two actuated degrees of freedom using regenerative kinetics, 2008.

Bergelin et al., Design of an active ankle-foot prosthesis utilizing a four-bar mechanism, 2012.

Eilenberg et al., Control of a Powered Ankle-Foot Prosthesis Based on a Neuromuscular Model, 2010.

European Office Action for EP Application No. 13713007.6, dated Feb. 10, 2016.

Hansen et al., Net external energy of the biological and prosthetic ankle druing gait initiation, 2010.

Hansen et al., The human ankle during walking: implications for design of biomimetic ankle prostheses, 2004.

Hitt et al., An active foot-ankle prosthesis with biomechanical energy regeneration, 2010.

Holgate, et al., Control Algorithms for ankle robots: a reflection on the state-of-the-art and presentation of two novel algorithms, 2008.

Huff et al., Preliminary Evaluation of a Walking Controller for a Powered Ankle Prosthesis (2013).

International Search Report and Written Opinion dated Apr. 23, 2014, for PCT Application No. PCT/US2013060110.

International Search Report and Written Opinion dated Jun. 28, 2013, for PCT Application No. PCT/US2013/031286.

International Search Report and Written Opinion dated Aug. 18, 2016, for PCT Application No. PCT/US2016/021074.

Iwalk, in The News FAQ, Aug. 12, 2011.

Jinying et al., PANTOE 1: Biomechanical design of powered ankle-foot prosthesis with compliant joints and segmented foot, 2010.

Klute, et al. Muscle-like pneumatic actuators for below-knee prostheses, 2000.

McCluney, Walter Reed Patients Test Next Generation Prosthesis, Dec. 10, 2009.

Molen, et al., Energy/speed relation of below-knee amputees walking on a motor-driven treadmill, 1973.

Non-Final office action dated Dec. 31, 2012 for U.S. Appl. No. 13/115,175.

Non-Final office action dated May 13, 2011, for U.S. Appl. No. 12/427,384.

Final office action dated Oct. 13, 2011, for U.S. Appl. No. 12/427,384.

Non-Final office action dated Jan. 3, 2013, for U.S. Appl. No. 12/427,384.

Novacheck, The biomechanics of running, 1998.

Power Knee, 2010.

Prosthetics, Hydracadence Knee; Handicap Technology, Aug. 12, 2011.

Shorter, A portable powered ankle-foot orthosis for rehabilitation, 2011.

Sup et al. Design of a Pneumatically Actuated Transfemoral Prosthesis, 2006.

Torburn et al., Energy expenditure during ambulation in dysvascular and traumatic below-knee amputees, 1995.

Winter, the biomechanics and Motor Control of Human Gait, 1991.

Zen Chirpractic, Gait Analysis: You can run, but you can not hide!, May 9, 2016.

\* cited by examiner

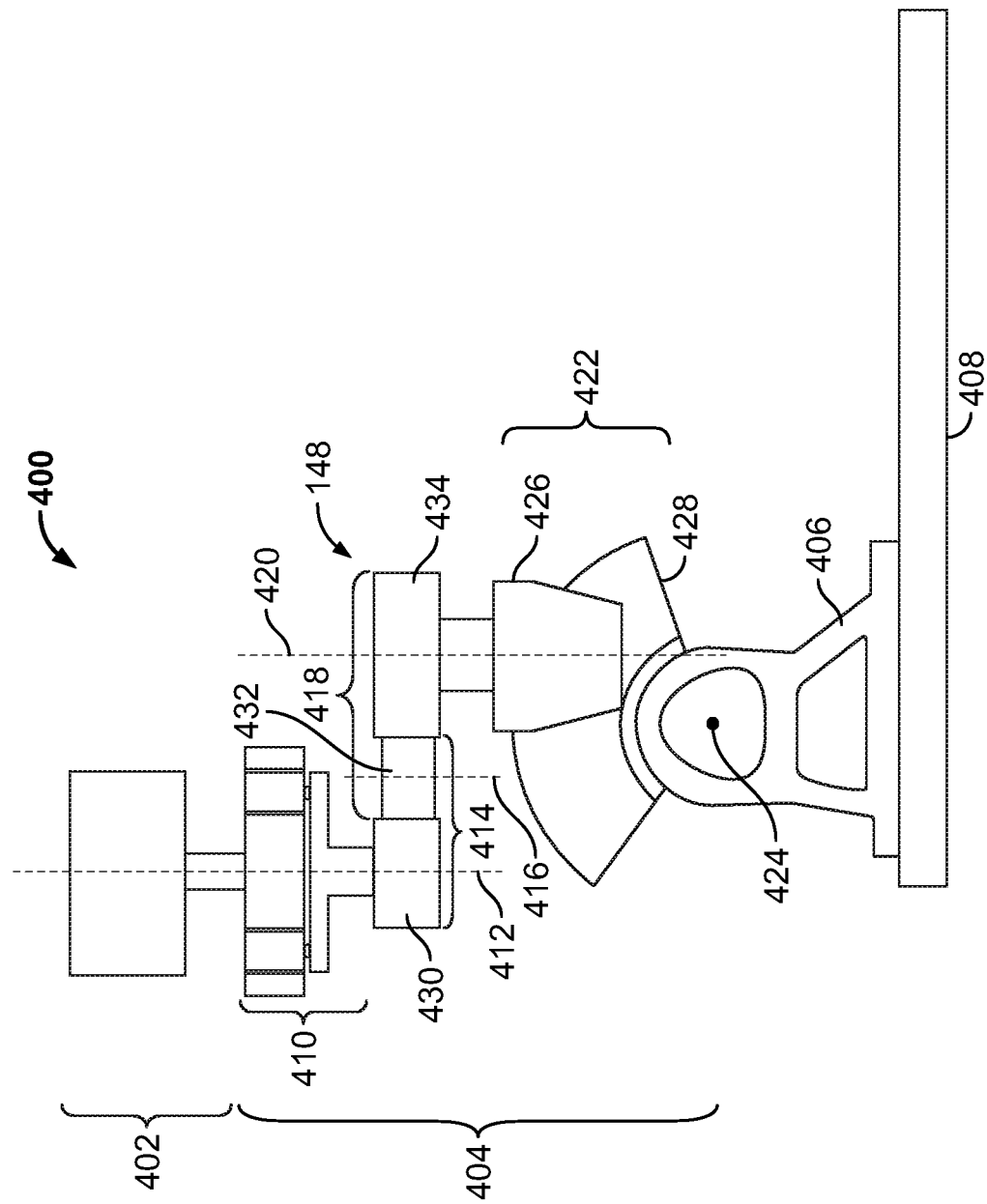

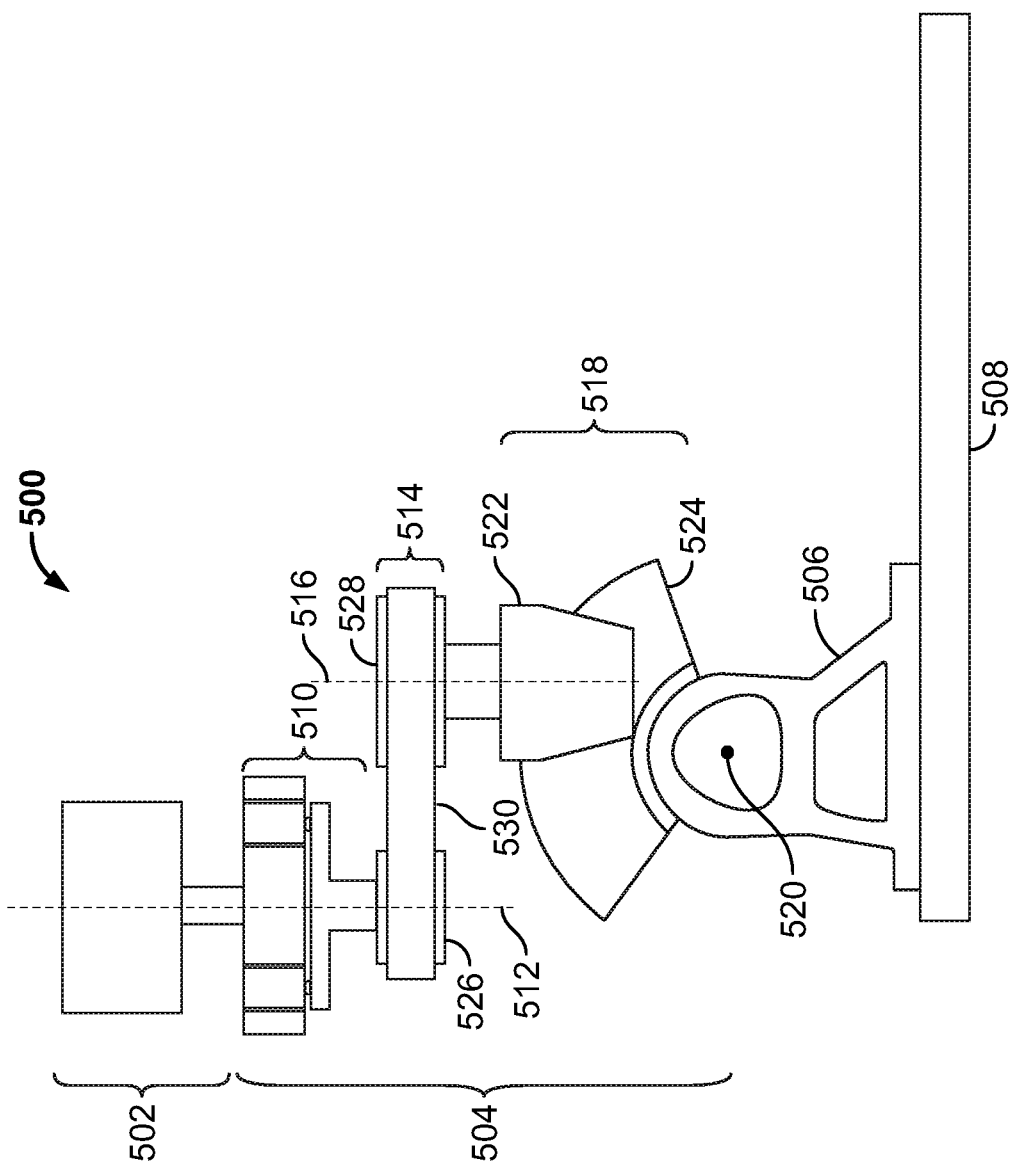

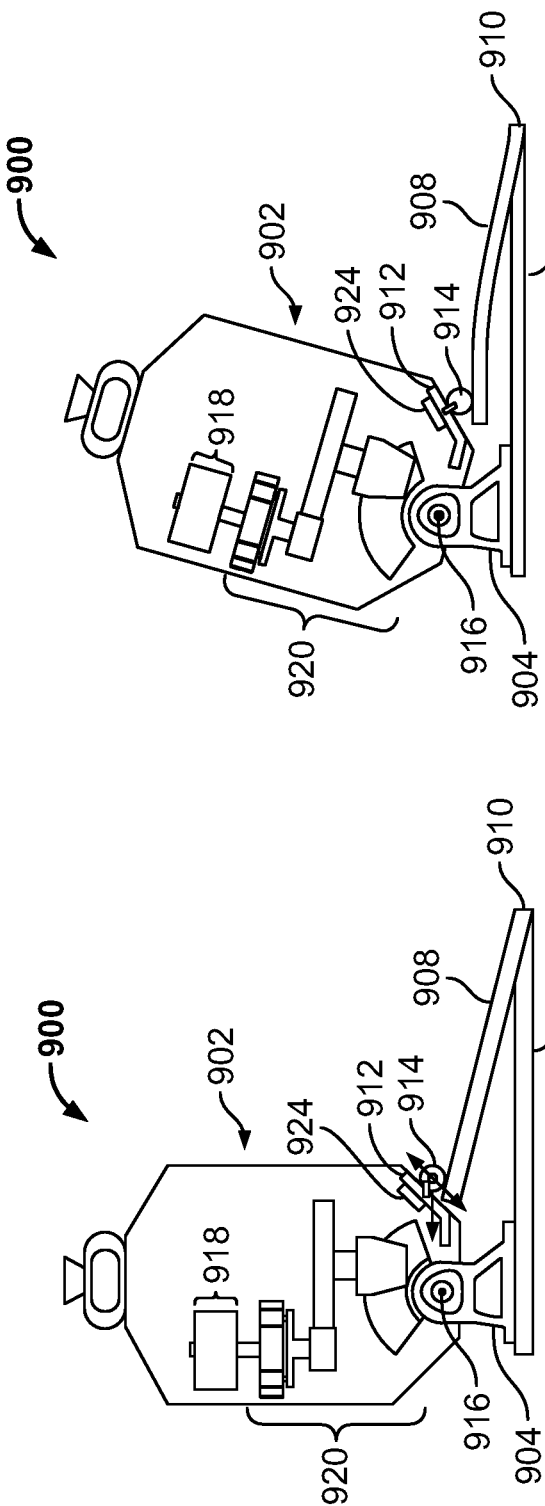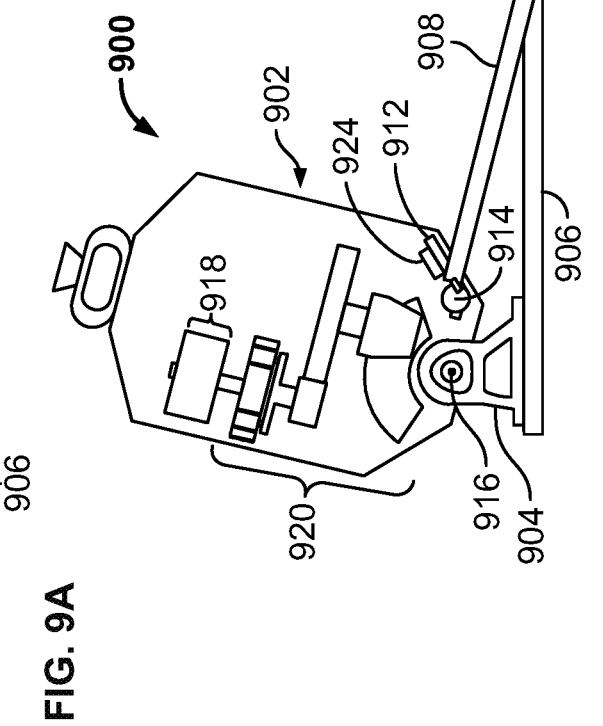

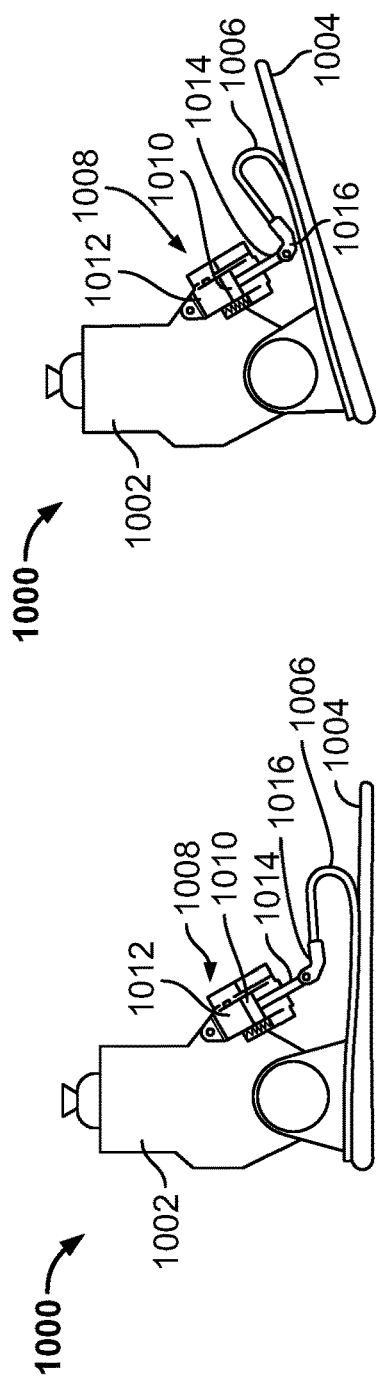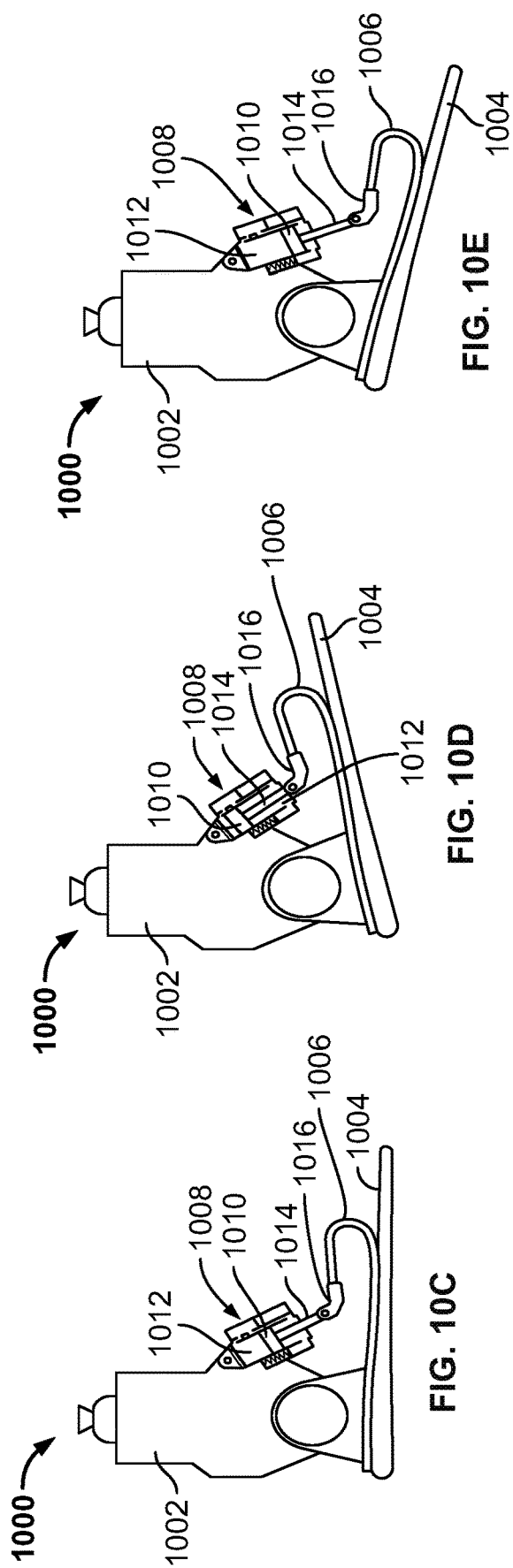

LOWER LIMB PROSTHESIS

CROSS-REFERENCE TO RELATED APPLICATIONS

This application is a continuation of PCT/US2016/021074, filed Mar. 4, 2016, which claims priority to U.S. Provisional Application Ser. No. 62/128,371, filed on Mar. 4, 2015, each of which is hereby incorporated by reference in its entirety.

FIELD

The embodiments herein relate to lower limb prostheses configured to simulate certain capabilities of an intact human ankle.

BACKGROUND

Until recently, lower limb prostheses were generally passive devices controlled by a user's own motion. Currently, some lower limb prostheses allow for plantar flexion and dorsiflexion movement of a foot member about a joint axis. In addition, microprocessor control (MPC) has been introduced to better mimic the motion of a natural foot and ankle. In MPC prostheses, the microprocessor controls an amount of damping or stiffness in moving a foot member and/or control the lower limb prosthesis to actively propel the user forward while walking. While such lower limb prostheses may provide a more natural motion, design challenges remain. For example, the addition of components that provide new or improved functionality may increase the size, weight, and/or power requirements of the lower limb prostheses. These factors may limit the population, such as pediatric patients, for example, that may benefit from the prostheses because they require a user to exert more energy while walking, and/or decrease the use time between battery charges, which are not suitable for smaller or weaker patients. Thus, a need exists for new lower limb prostheses that offer advantages over standard lower limb devices.

BRIEF SUMMARY

In one embodiment, a lower limb prosthesis is provided, comprising a foot member, and a main body rotatably coupled to the foot member at a joint comprising a joint axis, wherein the main body comprises a housing, an actuator, and a transmission comprising at least one intermediate stage and a final stage, and wherein the actuator is configured to transmit an actuator torque to the transmission, the at least one intermediate stage is configured to transmit an intermediate torque about an intermediate axis, and the final stage is configured to transmit a final torque about the joint axis to the foot member. The main body may be rotatably coupled to the foot member through a foot coupler, and wherein the final torque may be transmitted to the foot member via the foot coupler. The at least one intermediate stage comprises a first intermediate stage and a second intermediate stage may be engaged with the first intermediate stage, wherein the first intermediate stage may be configured to transmit a first intermediate torque about a first intermediate axis and the second intermediate stage is configured to transmit a second intermediate torque about a second intermediate axis. A direction vector of the first intermediate axis and a direction vector of the second intermediate axis may be parallel or perpendicular to a direction vector of the joint axis. The at least one intermediate stage may comprise a first intermediate stage and a second intermediate stage engaged with the first intermediate stage, wherein the first intermediate stage is configured to transmit a first intermediate torque about the intermediate axis and the second intermediate stage is configured to transmit a second intermediate torque about the same intermediate axis. The first intermediate stage may be an epicyclic stage and the second intermediate stage comprises spur or helical gears, or comprises a belt and a pulley, or a chain and a sprocket, or comprises a second a second epicyclic stage. The first epicyclic stage may have a planetary configuration and the second epicyclic stage may have a star configuration. Alternatively, the first intermediate stage may comprises a belt and a pulley, or a chain and a sprocket, and the second intermediate stage comprises a belt and a pulley, or a chain and a sprocket. The final stage may comprise a hypoid gear. The at least one intermediate stage may further comprise a third intermediate stage configured to transmit a third intermediate torque about a third intermediate axis, and wherein the direction vectors of the first intermediate axis, the second intermediate axis, and the third intermediate axis are perpendicular to the direction vector of the joint axis. The lower limb prosthesis may further comprise a controller and a sensor, wherein the controller receives prosthetic information from the sensor, and wherein the controller is configured to use at least the prosthetic information to control the actuator. The sensor may comprise an absolute encoder, and the prosthetic information comprises a position signal indicating an angular position of the foot member relative to the main body. The at least a portion of the absolute encoder may be positioned on the final stage of the transmission. The sensor may comprise an incremental encoder, and the prosthetic information comprises an incremental signal indicating a change in an angular position. The incremental encoder may be located on the actuator, and the angular position may be an angular position of a rotor of the actuator. The incremental encoder may be located on an intermediate stage of the at least one intermediate stage, and the angular position may be an angular position of a shaft of the intermediate stage. The sensor may comprise a torque sensor, and the prosthetic information may comprise a torque signal indicating the final torque. At least a portion of the torque sensor may be located on a foot coupler fixedly attached to the foot member, and wherein the final torque may be transmitted to the foot member via the foot coupler. The at least one sensor may comprise a force sensor, and the prosthetic information may comprise a force signal indicating a force applied to the foot member. The at least one sensor may comprise an inertial measurement unit, and the prosthetic information may indicate at least one of a velocity, acceleration, or orientation of at least a portion of the lower limb prosthesis.

In another embodiment, a lower limb prosthesis may be provided, comprising a foot member, a main body rotatably coupled to the foot member at a joint comprising a joint axis, wherein the main body comprises a housing, an actuator, and a transmission, and wherein the actuator is configured to transmit a actuator torque to the transmission, and the transmission is configured to transmit a final torque to the foot member, and a spring coupled to the foot member and the main body, wherein the spring is configured to apply a spring force to the foot member, and wherein the spring force acts in parallel to the final torque. The lower limb prosthesis may further comprise an engagement mechanism, wherein the engagement mechanism is configured to engage and disengage the spring. In some variations, when the spring is engaged, the spring may be configured to apply the spring force to the foot member, and when the spring is disengaged, the spring may be not configured to apply the spring force to the foot member. When the spring is engaged, the spring may engage the main body at an engagement position. The engagement mechanism may be further configured to adjust the engagement position. Adjusting the engagement position may change a neutral position of the lower limb prosthesis, and wherein the neutral position of the lower limb prosthesis is an angular position of the foot member relative to the main body at which the engaged spring is in equilibrium. The lower limb prosthesis may further comprise a controller in electronic communication with the engagement mechanism, wherein the engagement mechanism is configured to engage the spring, disengage the spring, and adjust the engagement position in response to a signal from the controller. The lower limb prosthesis may further comprise an engagement position sensor configured to provide an engagement position signal to the controller indicating the engagement position of the spring. The lower limb prosthesis may further comprise a torque sensor configured to provide a torque signal to the controller, wherein the controller is configured to control the engagement mechanism in response to the torque signal. The lower limb prosthesis may further comprise an absolute encoder configured to provide a position signal to the controller indicating the position of the foot member relative to the main body, and wherein the controller is configured to control the engagement mechanism in response to the position signal. The engagement mechanism may comprise a track, and wherein a portion of the spring is configured to slide along the track and reversibly lock into an engagement position on the track. The engagement mechanism may comprise a chamber at least partially filled with a hydraulic fluid, a piston within the chamber, wherein the piston separates the chamber into a first side and a second side, a piston rod connecting the piston to the spring, and a valve fluidly connected to the first side and the second side, wherein the valve is configured to be opened to allow hydraulic fluid to move between the first side and the second side and closed to block hydraulic fluid from moving between the first side and the second side, and wherein the piston is slidable within the chamber when the valve is open and fixed relative to the chamber when the valve is closed. The spring may be in the engaged state when the valve is closed, and the spring may be in the disengaged state when the valve is open. The valve may be a solenoid valve. The lower limb prosthesis may further comprise a reservoir configured to contain a variable volume of hydraulic fluid in order to compensate for changes in a volume of hydraulic fluid in the chamber.

In still another embodiment, a lower limb prosthesis is provided, comprising a foot member, a main body rotatably coupled to the foot member at a joint comprising a joint axis, and a combined spring and engagement mechanism coupled to the foot member and the main body, wherein the combined spring and engagement mechanism is configured to apply a force to the foot member and the main body. The combined spring and engagement mechanism may comprise a chamber at least partially filled with a compressed gas and a piston slidably disposed within the chamber, and wherein the piston is configured to separate the chamber into a first side and a second side. The combined spring and engagement mechanism may further comprise a valve fluidly connected to the first side and the second side of the chamber, and wherein the valve is configured to be opened to allow the compressed gas to move between the first side and the second side and closed to block the compressed air from moving between the first side and the second side. The combined spring and engagement mechanism may be engaged when the valve is closed, and the combined spring and engagement mechanism may be disengaged when the valve is open. When the combined spring and engagement mechanism is engaged, the combined spring and engagement mechanism may be configured to apply a spring force to the foot member.

BRIEF DESCRIPTION OF THE DRAWINGS

FIG. 4 is a schematic representation of another variation of a lower limb prosthesis with a transmission.

FIG. 5 is a schematic representation of another variation of a lower limb prosthesis with a transmission.

FIGS. 9A-9C are schematic representations of a variation of a lower limb prosthesis comprising a spring under different conditions.

FIGS. 10A-10K are side views of a variation of a lower limb prosthesis in various positions.

DETAILED DESCRIPTION

Figure 1:
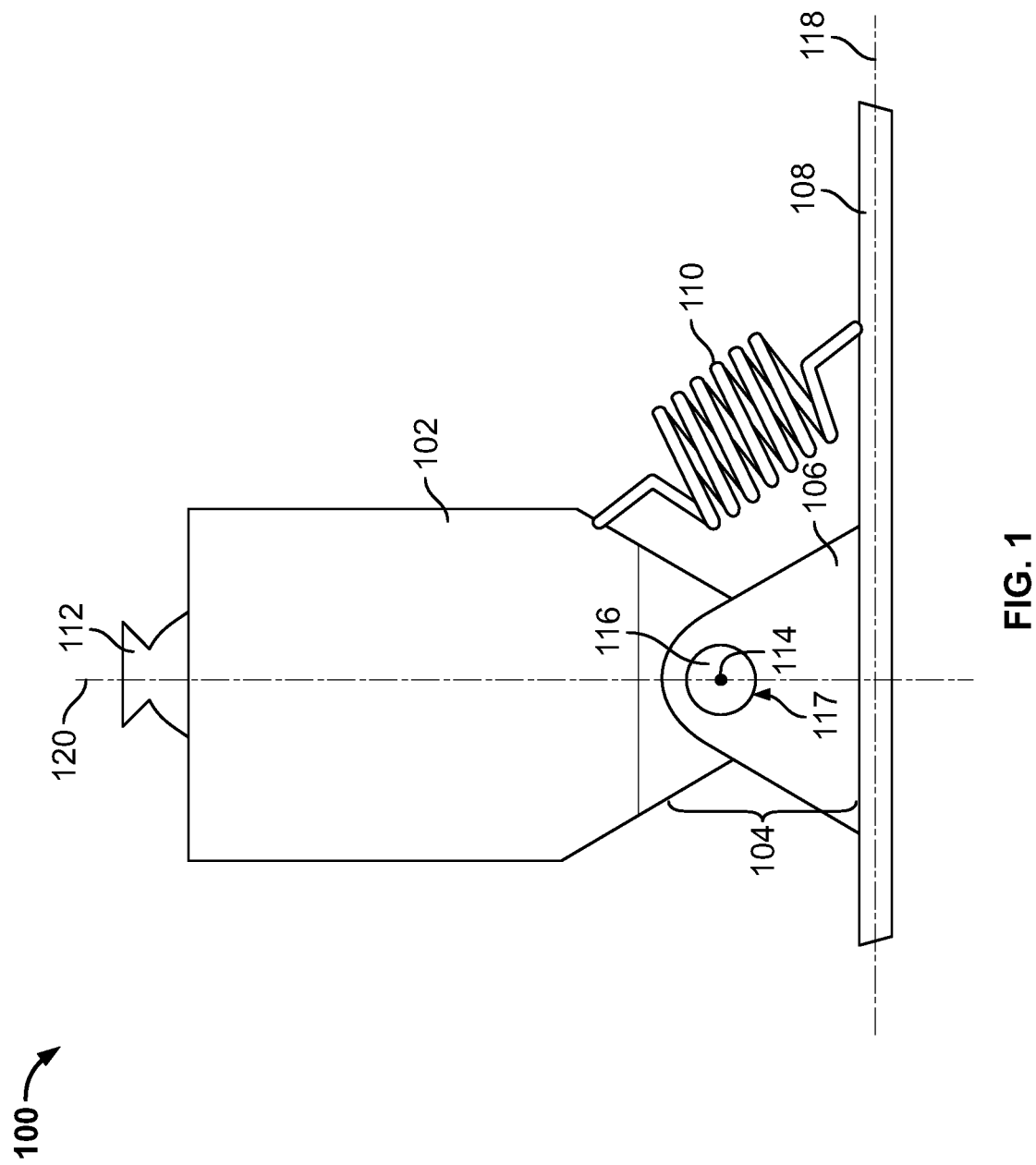
FIG. 1 is a schematic representation of a lower limb prosthesis.

The features and advantages of the embodiments of the present disclosure will become more apparent from the detailed description set forth below when taken in conjunction with the drawings. The drawings and the associated descriptions are provided to illustrate embodiments of the disclosure and not to limit the scope of what is claimed.

In the following detailed description, numerous specific details are set forth to provide a full understanding of the present disclosure. It will be apparent, however, to one of ordinary skill in the art that the various embodiments disclosed may be practiced without some of these specific details. In other instances, well-known structures and techniques have not been shown in detail to avoid unnecessarily obscuring the various embodiments. It should also be understood that embodiments of lower limb prostheses may comprise any combination of features described with respect to the variations of lower limb prostheses disclosed herein.

Lower Limb Prosthesis

Described herein are lower limb prostheses that may be configured to simulate certain capabilities of an intact human ankle. For example, the lower limb prostheses may provide energy to actively propel a user during ambulation and/or allow a user to efficiently ambulate over uneven terrains. The lower limb prostheses may comprise a main body and a foot member that may be configured to rotate relative to one another at a joint. The location of the joint may be similar to the location of a natural ankle joint. In some variations, the lower limb prostheses may comprise a foot coupler that may be coupled to the foot member and may engage a portion of the main body, thereby coupling the foot member to the main body. The lower limb prostheses may be configured to attach to a pylon or otherwise connect to a socket on a user's residual limb, such as with a pyramid that may be positioned on a proximal end of the lower limb prostheses.

The lower limb prostheses may be configured to actively dorsiflex and/or plantarflex. For example, the lower limb prostheses may comprise a power source, such as a battery, an actuator or motor, and a transmission. At least some of these elements may be positioned in or on a housing of the main body. The motor, which may be a brushless DC motor, may drive the transmission, and an output of the transmission may apply a torque to the foot member. The transmission may, for example, provide a mechanical advantage by amplifying a torque produced by the actuator. Additionally or alternatively, the transmission may change an angular velocity and/or an orientation of an axis of rotation between an input to the transmission and an output from the transmission. The transmission may comprise one or more stages (e.g., one or more intermediate stages and a final stage) in order to produce a desired torque and angular velocity. In some variations, at least one intermediate stage may be an epicyclic stage with a planetary or a star configuration. In still other variations, the prosthesis may comprise a direct drive system, without a transmission, with the motor connected directly to the movable member.

In some variations, the lower limb prostheses may comprise a spring that may act in parallel to a torque produced by the actuator and transmitted by the transmission. For example, the spring may be coupled to the main body and the foot member, and it may be configured to provide energy during the push off stage of the gait cycle. In some variations the spring may be coupled to the main body or the foot member through an engagement mechanism, which may adjust how the spring interacts with the lower limb prosthesis. For example, the engagement mechanism may engage or lock the spring, allowing the spring to store and provide energy, and disengage or unlock the spring, such that the spring does not store and provide energy. Additionally or alternatively, the engagement mechanism may adjust a position of a portion of the spring relative to the main body. In this way, the spring may be adjusted to store and provide energy at the most advantageous times during the gait cycle regardless of the incline of the ground or the heel height of the foot member.

In some variations, the lower limb prostheses may comprise a controller that may be configured to control one or more elements of the lower limb prostheses. The controller may comprise, for example, a memory and a processor configured to execute instructions stored in the memory. The controller may control the lower limb prosthesis, at least partially, based on prosthetic information that is detected and provided to the controller by one or more sensors. The lower limb prostheses may comprise one or more types of sensors, each of which may detect information about a current state of the prostheses. For example, the lower limb prostheses may comprise an absolute encoder to detect an angular position of the foot member relative to the main body, an incremental encoder to detect changes in an angular position of a component of the transmission, an inertial measurement unit to detect acceleration and velocity of the lower limb prostheses, and/or a torque sensor to measure a torque exerted on the foot member. The controller may use the prosthetic information provided by one or more sensors, for example, to determine the phase of gait, control the actuator output, and/or control the engagement mechanism.

FIG. 1 is a schematic representation that illustrates basic mechanical components of a lower limb prosthesis. As shown, lower limb prosthesis 100 may comprise main body 102, foot member 108, spring 110, and pyramid 112. In use, main body 102 may have a similar location to an anatomical shank of a natural lower leg, and it may support the weight of a user. Main body 102 may comprise a housing, an actuator, a transmission, and a controller (not shown). Main body 102 may be rotatably coupled to foot member 108 at joint 104, which may comprise joint axis 114. Put another way, joint 104 may be configured to allow rotation between foot member 108 and main body 102 about joint axis 114. In some variations, joint 104 may be configured to transmit a torque from main body 102 (e.g., from a transmission of main body 102) to foot member 108. In some variations, a portion of main body 102 and a portion of foot member 108 may form joint 104 such that main body 102 and foot member 108 are directly coupled. In other variations, an element attached to main body 102 and/or an element attached to foot member 108 may form joint 104 such that main body 102 and foot member 108 are indirectly coupled.

As shown in FIG. 1, joint 104 may be formed by output shaft 116 of the transmission, which may be housed in or on main body 102, and foot coupler 106, which may be attached to or integrally formed with foot member 108. In some variations, output shaft 116 may be at least partially positioned within opening 117 of foot coupler 106 in order to rigidly attach output shaft 116 and foot coupler 106. In use, the actuator may produce an actuator torque that is applied to the transmission, and the transmission may produce a final torque that is applied to foot member 108 via output shaft 116 and foot coupler 106. The final torque may be applied about joint axis 114, which may result in rotation of foot member 108 and main body 102 relative to one another. Rotation of foot member 108 and main body 102 relative to one another may change an angle between foot member 108 and main body 102, for example, the angle between longitudinal axis 118 of foot member 108 and longitudinal axis 120 of main body 102.

As mentioned above, lower limb prosthesis 100 may comprise spring 110. Spring 110 may be at least temporarily coupled to main body 102 and foot member 108 directly or indirectly and may be configured to store energy and subsequently release the energy to apply a spring force to foot member 108. For example, spring 110 may be configured to store energy when it is compressed and/or strained, and release energy as it extends back toward equilibrium. In some variations, spring 110 may be configured to act in parallel to a torque produced by the actuator and transmitted by the transmission. In other words, the spring force applied by spring 110 to foot member 108 may produce a torque about the same joint axis 114 as the torque produced by the actuator and transmitted by the transmission. Thus, the torque produced by the spring force and the torque transmitted by the transmission may be additive. While FIG. 1 depicts lower limb prosthesis 100 with a singular spring, it should be appreciated that some variations of lower limb prosthesis 100 may comprise more than one spring (e.g., two, three, four, or more), or may not comprise a spring at all. Moreover, while spring 110 is depicted as a coil spring, in other variations spring 110 may comprise a lever spring, an air piston or gas spring, or any other spring mechanism capable of storing a desired amount of energy. In the embodiment depicted in FIG. 1, spring 110 is attached proximally to a lower portion of housing 102 and distally foot member 108, at locations anterior to joint axis 114. In other embodiments, a spring may be provided wherein the proximal and/or distal attachments are located posterior to joint axis 114.

As shown in FIG. 1, lower limb prosthesis 100 may comprise pyramid 112, which may be positioned at a proximal end of main body 102. Pyramid 112 may be integrally formed with main body 102 or attached to main body 102 with fasteners such as screws, bolts, and/or the like. Pyramid 112 may facilitate the releasable coupling of lower limb prosthesis 100 to a user. For example, pyramid 112 may be configured to at least temporarily couple to a pylon or other element connected to a socket on a residual limb of a user. In some variations, pyramid 112 may be configured to couple lower limb prosthesis 100 to another prosthetic device, such as a prosthetic knee.

Pyramid 112 may comprise standard or custom female and/or male components to facilitate coupling of lower limb prosthesis 100 to another component or device. In some variations, pyramid 112 may comprise one or more openings or ports through which one or more cables or connectors may pass (e.g., a cable connecting an external power source to an element within main body 102). In some variations, however, lower limb prosthesis 100 may not comprise pyramid 112. For example, lower limb prosthesis 100 may comprise another attachment mechanism or lower limb prosthesis 100 may be integrated into another device, such as a combined prosthetic knee and ankle device.

Main Body

Figure 2:
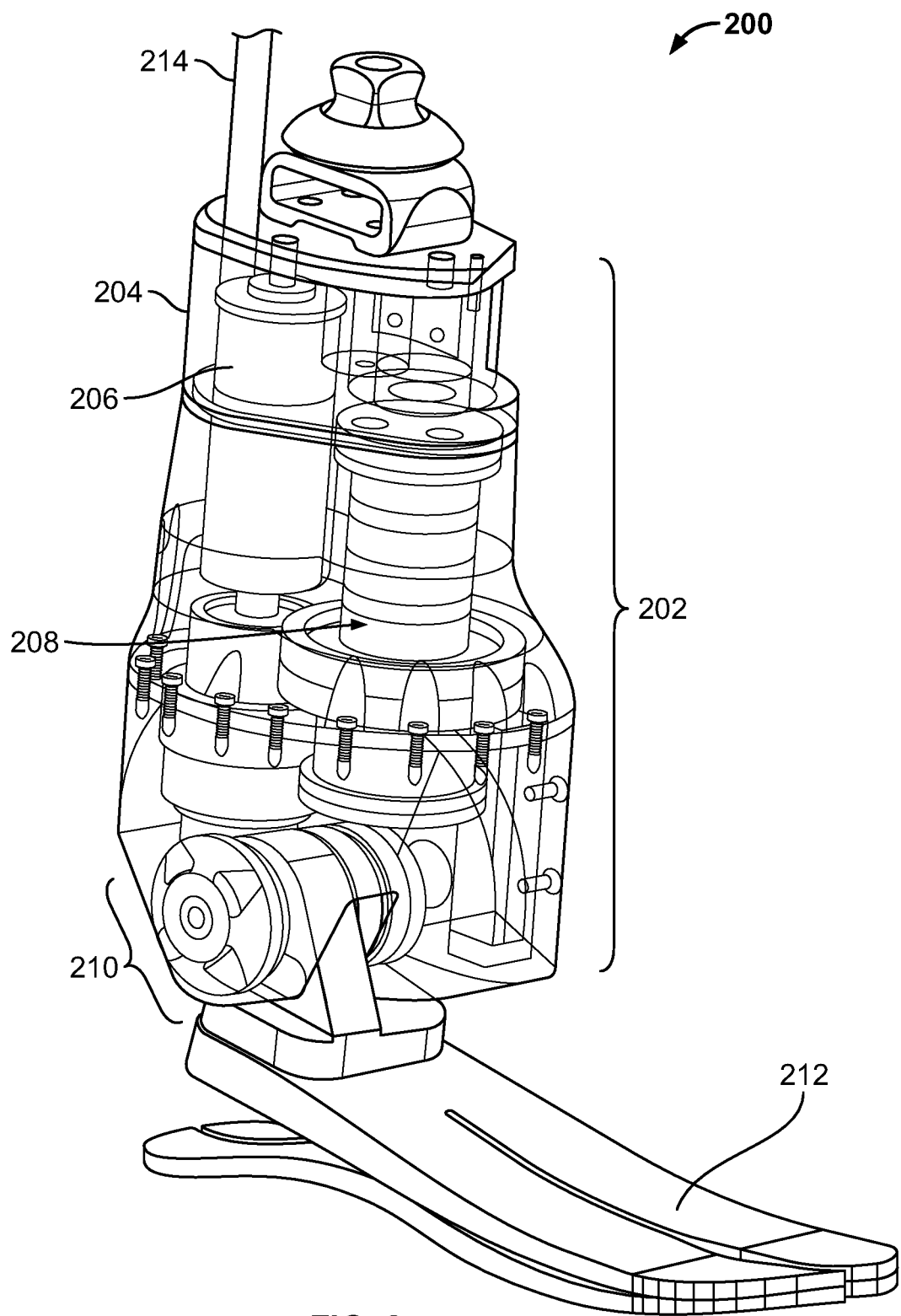
FIG. 2 is an isometric view of a variation of a lower limb prosthesis, with the housing depicted in semi-transparency to show the internal components.

FIG. 2 is an isometric view of a variation of a lower limb prosthesis that illustrates details of a main body. As shown, lower limb prosthesis 200 may comprise main body 202, which is rotatably coupled to foot member 212 at joint 210. In use, main body 202 may be positioned at a location similar to the location of the shank of a natural lower leg, i.e., below the knee and above the ankle. Main body 202 may be configured to support the weight of a user while also comprising at least some of the elements responsible for the control and movement of lower leg prosthesis 200. For example, main body 202 may comprise housing 204, actuator 206, and transmission 208. In some variations, main body 202 may also comprise a power source, such as a battery, a controller, circuitry, and/or one or more sensors (not shown). As will be described in detail herein, joint 210 may comprise a portion of main body 202, such as a portion of transmission 208, in order to facilitate rotation of main body 202 and foot member 212 relative to one another.

Housing

As shown in FIG. 2, housing 204 covers and/or supports other elements of main body 202 (e.g., actuator 206, transmission 208, a controller, a power source, one or more sensors, and circuitry). Housing 204 may comprise one or more compartments in which one or more elements of main body 202 may be at least partially contained. In some variations, one or more compartments of housing 204 may be sealed, such as hermetically sealed or sealed watertight (i.e., the one or more compartments may be waterproof). It may be advantageous for housing 204 to comprise at least one sealed compartment in order to protect one or more elements of main body 202 from damage, such as water damage, and/or to keep lubricating fluid, such as lubricating fluid for elements of transmission 208, contained in housing 204. In some variations, at least a portion of one or more elements of main body 202 may be mounted or otherwise attached to an interior surface or an exterior surface of housing 204. Additionally or alternatively, at least a portion of one or more elements of main body 202 may be integrated into a structure of housing 204, such as circuitry and/or one or more sensors. In some variations, one or more elements may have a portion inside of housing 204 and a portion outside of housing 204, such as electrical cable 214, which may connect actuator 206 to a power source that is external to main body 202. In these and other variations, housing 204 may comprise one or more openings and/or ports for passage of the elements therethrough. These openings and/or ports may optionally be sealed.

Housing 204 may be configured to support the weight of a user and to protect elements inside of housing 204 from damage if housing 204 is hit or otherwise contacted. However, the housing 204 may be light enough to prevent a user and/or actuator 206 from exerting unnecessary energy to propel lower limb prosthesis 200 during ambulation. Suitable materials for housing 204 may include, but are not limited to titanium, stainless steel, aluminum alloys, carbon fiber, plastic and the like, or any combination thereof. In some variations, an outer shape, total volume, and/or profile of housing 204 may be similar to that of a natural human shank.

Actuator

Figure 3:
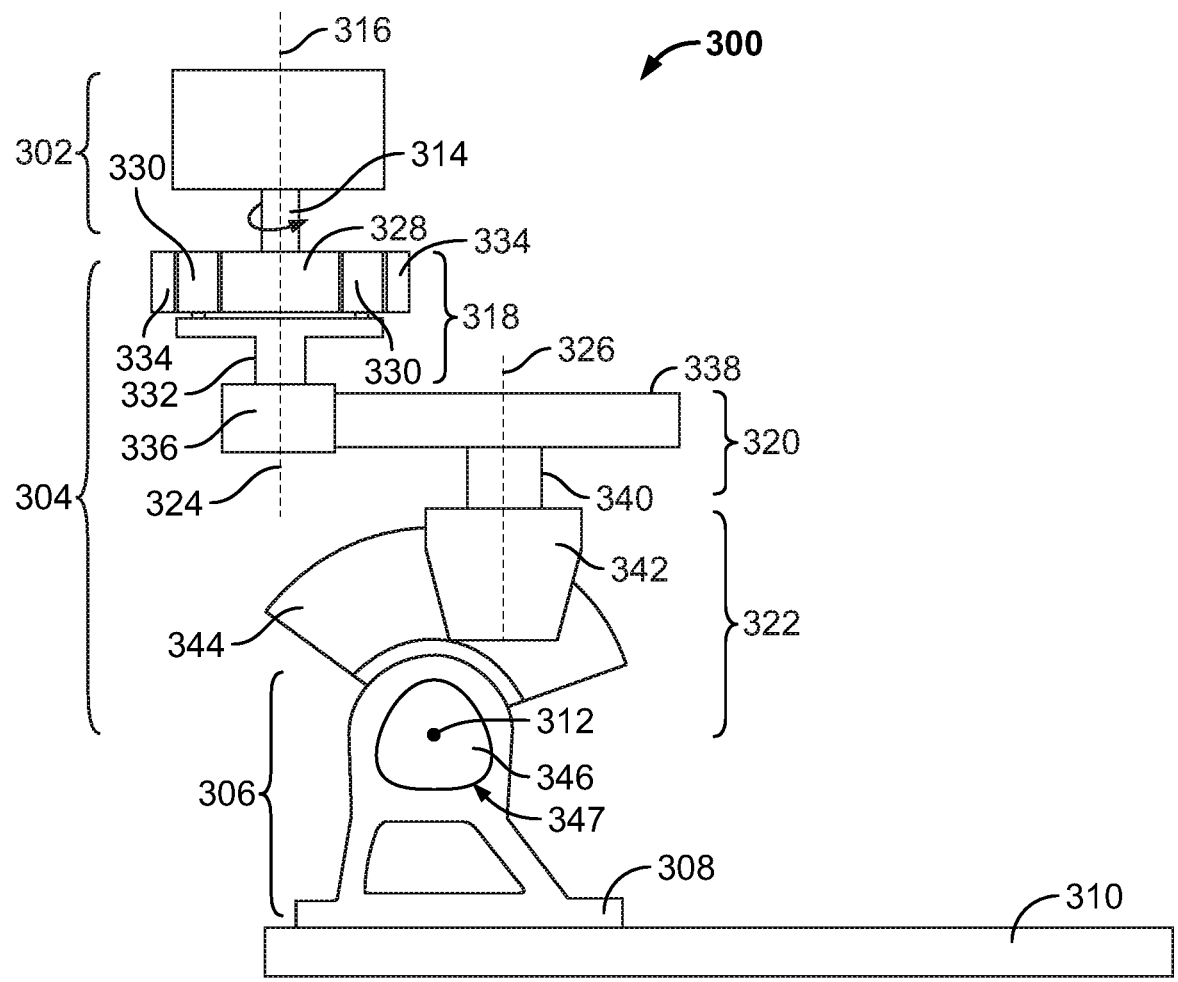
FIG. 3 is a schematic representation of a variation of a lower limb prosthesis with a transmission.

FIG. 3 is a schematic representation of a variation of a lower limb prosthesis with a housing removed to illustrate details of an actuator and a transmission. As shown, lower limb prosthesis 300 may comprise actuator 302, transmission 304, joint 306, foot coupler 308, and foot member 310. Actuator 302 may comprise any suitable motor that may produce a force or torque that is transmitted directly or indirectly, such as via transmission 304, to foot member 310 in order to produce rotation about joint axis 312. For example, in some variations, actuator 302 may comprise a brushless DC motor that comprises a stator and a rotor. Actuator 302 may or may not comprise one or more springs or other elastic elements to store elastic energy.

Actuator 302 may be coupled to transmission 304 such that a torque produced by actuator 302 may be transmitted to transmission 304. For example, a rotor of actuator 302 may be coupled to transmission 304 via actuator shaft 314. Actuator shaft 314 may apply an actuator torque about actuator axis 316 to an input of transmission 304. In some variations, actuator 302 may be configured to apply an actuator torque in only one direction (e.g., actuator shaft 314 may rotate only in a first direction about actuator axis 316). In other variations, actuator 302 may be configured to apply an actuator torque in two directions (e.g., actuator shaft 314 may rotate in a first direction and a second, opposite direction about actuator axis 316, actuator shaft 314 may rotate forwards and backwards, actuator shaft 314 may rotate clockwise and counterclockwise). It may be advantageous for actuator 302 to be configured to apply an actuator torque in two directions, as applying a torque in a first direction may cause dorsiflexion of foot member 310, and applying a torque in a second direction may cause plantar flexion of foot member 310.

Transmission

A main body of a lower limb prosthesis may comprise a transmission having one or more stages to transmit a torque produced by an actuator to a foot member. The transmission may modify the torque produced by the actuator in one or more ways such that a torque applied to the foot member by the transmission may have different properties than the torque produced by the actuator. For example, the transmission may provide a mechanical advantage by amplifying the torque produced by the actuator in order to apply a greater torque to the foot member. In some variations, the transmission may affect (e.g., increase or decrease) an angular velocity of an actuator shaft such that it may be different than the angular velocity of the foot member relative to the main body. In some variations, the transmission may change a direction of rotation (e.g., between counterclockwise and clockwise) such that the direction of rotation about an actuator axis may be different (e.g., the opposite) than the direction of rotation about the joint axis. Additionally or alternatively, the transmission may change an orientation of an axis of rotation (e.g., rotate an axis, for example, from vertical to horizontal) such that an orientation of the actuator axis of rotation may be different than an orientation of the joint axis.

Returning to FIG. 3, transmission 304 may comprise first intermediate stage 318, second intermediate stage 320, and final stage 322. Actuator 302 may be engaged with first intermediate stage 318, first intermediate stage 318 may be engaged with second intermediate stage 320, second intermediate stage 320 may be engaged with final stage 322, and final stage 322 may be engaged directly with foot coupler 308 and indirectly with foot member 310. In some variations, actuator 302 and transmission 304 may be continuously engaged with each other and with foot member 310 (i.e., actuator 302, transmission 304, and foot member 310 may not become disengaged during use of lower limb prosthesis 300). The actuator 302, intermediate stages 318 and 320, and final stage 322 may be engaged in any suitable manner, for example, by the meshing of gear teeth, contact of one element with another, direct or indirect coupling of one element to another, or the like.

Each stage of transmission 304 may comprise an input, a transmission element that receives a torque from another stage or from actuator 302, and an output, a transmission element that applies a torque to another stage or to foot member 310. It may be advantageous for transmission 304 to comprise multiple stages, as this may allow transmission 304 to better control the specific torque that is applied to foot member 310 and the resulting angular velocity of foot member 310 relative to the main body. While two intermediate stages, intermediate stages 318 and 320, are shown in FIG. 3, other variations of lower limb prostheses may comprise any suitable number of intermediate stages (e.g., 1, 2, 3, 4, 5 or more).

Actuator 302 may transmit an actuator torque to first intermediate stage 318 about actuator axis 316, and in turn, each stage of transmission 304 may transmit a torque about an axis of rotation. For example, in response to the actuator torque, first intermediate stage 318 may transmit a first intermediate torque to second intermediate stage 320 about first intermediate axis 324. In response to the first intermediate torque, second intermediate stage 320 may transmit a second intermediate torque to final stage 322 about second intermediate axis 326. In response to the second intermediate torque, final stage 322 may transmit a final torque to foot coupler 308 about joint axis 312.

Axes of rotation of a lower limb prosthesis (e.g., an axis of rotation of an actuator shaft, of an intermediate transmission stage, of a joint) may have any suitable spatial relationship to one another. For example, two or more axes of rotation may be the same or aligned, or in contrast, two or more axes of rotation may be different or off-set. Returning to FIG. 3, actuator axis 316 and first intermediate axis 324 may provide an example of two axes of rotation that may be the same or aligned. In other words, actuator 302 and first intermediate stage 318 may transmit torque about the same axis of rotation. In contrast, first intermediate axis 324, second intermediate axis 326, and joint axis 312 may provide an example of axes of rotation that may be different or off-set. It should be appreciated that FIG. 3 depicts only one variation of spatial relationships of axes of rotation, and any axes of rotation of a lower limb prosthesis (e.g., actuator axis, axis of an intermediate transmission stage, joint axis) may be aligned or off-set.

Axes of rotation of a lower limb prosthesis (e.g., an axis of rotation of an actuator shaft, of a transmission stage, of a joint) may also have any suitable angular relationship to one another. For example, two or more axes of rotation may be parallel, perpendicular, or neither (e.g., skew, transverse but not perpendicular). Returning to FIG. 3, actuator axis 316, first intermediate axis 324, and second intermediate axis 326 may provide an example of parallel or approximately parallel axes, whereas each of these axes may be perpendicular or approximately perpendicular to joint axis 312. The axes of rotation of other variations of lower limb prostheses may have other angular relationships. It should be appreciated that in some variations, the angular relationship between two or more axes may be described with direction vectors, which may allow the angular relationship to be described even if the two or more axes are in different planes. For example, each axis of rotation of a lower limb prosthesis may have a direction vector that may indicate the direction or orientation of the axis, similar to the slope of a line. When two axes of rotation are described as parallel, their direction vectors may be parallel, and when two axes of rotation are described as perpendicular, their direction vectors may be perpendicular. If perpendicular axes of rotation are in the same plane, then they may intersect and form right angles. However, if perpendicular axes of rotation are not in the same plane, then they may not intersect, but their direction vectors may still be perpendicular.

Orientating two or more axes of rotation to have certain spatial and/or angular relationships may provide one or more benefits. For example, configuring a lower limb prosthesis to have two or more axes of rotation that are aligned may be advantageous by decreasing a size of the lower limb prosthesis (e.g., a size of the main body, a volume of the main body) and/or allowing the lower limb prosthesis to occupy a desired overall shape or profile (e.g., allowing the main body to have a profile similar to a natural human shank). As another example, orientating one or more intermediate transmission stages to have an intermediate axis with a direction vector that is not parallel to the direction vector of the joint axis (e.g., skew or perpendicular) may be advantageous because doing so may decrease an overall height of the lower limb prosthesis and/or provide more space for components of the lower limb prosthesis. Decreasing the height of the lower limb prosthesis may, for example, allow it to be used by shorter adults and children in addition to taller adults.

As shown in FIG. 3, each stage of transmission 304 may be configured to transmit a torque using one or more transmission elements. The transmission elements may be gears (e.g., a spur gear, helical gear, herringbone gear, spiral bevel gear, hypoid gear, epicyclic gear, harmonic gear, or the like), pulleys, sprockets, belts, chains, or any other elements that may contribute to the transmission of a force or torque. For example, as depicted in FIG. 3, first intermediate stage 318 may be an epicyclic stage that comprises sun gear 328, one or more planet gears 330 connected to carrier 332, and annular gear 334. As shown, the epicyclic stage may have a planetary configuration. In other words, sun gear 328 may be the input of first intermediate stage 318 and may receive the actuator torque via actuator shaft 314. Rotation of sun gear 328 may result in rotation of one or more planet gears 330 around sun gear 328 and within annular gear 334. Annular gear 334 may be fixed relative to sun gear 328 and one or more planet gears 330. Carrier 332 may be coupled to one or more planet gears 330 such that rotation of one or more planet gears 330 around sun gear 328 may result in rotation of carrier 332 about first intermediate axis 324. Carrier 332 may be the output of first intermediate transmission stage 318 and may transmit a first intermediate torque about first intermediate axis 324 to second intermediate stage 320. While first intermediate stage 318 is shown as an epicyclic stage with a planetary configuration, it should be appreciated that the epicyclic stage may have other configurations, such as a star or a solar configuration, which will be discussed in detail with respect to FIG. 6.

Second intermediate stage 320 may comprise gear 336 and gear 338. Gear 336 may be the input of second intermediate stage 320 and may rotate in response to the first intermediate torque applied by carrier 332 of first intermediate stage 318. Rotation of gear 336 may drive rotation of gear 338. As with first intermediate stage 318, second intermediate stage 320 may comprise any suitable type of transmission element such as a spur gear, helical gear, herringbone gear, or the like. Gear 338 may be the output of second intermediate stage 320 and may transmit the second intermediate torque to final stage 322 about second intermediate axis 326. The second intermediate torque may be transmitted to final stage 322 via shaft 340.

As shown in FIG. 3, final stage 322 may comprise hypoid gears including hypoid pinion 342 and segmented hypoid ring gear 344. While the hypoid gears may comprise a complete hypoid ring gear in some variations, it may be advantageous for the hypoid ring gear to be segmented, as this may decrease the weight of the final stage and the volume that it occupies. Hypoid pinion 342 may be the input of final stage 322 and may rotate in response to the second intermediate torque transmitted via shaft 340. Rotation of hypoid pinion 342 may drive rotation of segmented hypoid ring gear 344. Segmented hypoid ring gear 344 may be the output of final stage 322 and may transmit a final torque about joint axis 312. As shown, segmented hypoid ring gear 344 may be coupled to or integrally formed with output shaft 346 of transmission 304. Output shaft 346 may engage foot coupler 308 at opening 347, and the final torque produced by segmented hypoid ring gear 344 may be transmitted to foot member 310 via output shaft 346 and foot coupler 308. The final torque may result in rotation of foot member 310 relative to the main body.

As shown in FIG. 3, the axis of rotation of hypoid pinion 342 may have a first orientation (e.g., vertical, parallel to a longitudinal axis of the main body), whereas the axis of rotation of segmented hypoid ring gear 344 may have a second orientation that is different than the first orientation (e.g., perpendicular to the axis of rotation of hypoid pinion 342, perpendicular to a longitudinal axis of the main body, horizontal). While hypoid gears are shown, final stage 322 may comprise any suitable gear type that may change the direction vector of an axis of rotation from the input to the output of the stage, including but not limited to bevel gears, spiral bevel gears, worm gears, or the like.

FIG. 4 is a schematic depiction of a side view of a variation of a lower limb prosthesis comprising a transmission with three intermediate stages and a final stage. As shown, lower limb prosthesis 400 may comprise actuator 402, transmission 404, foot coupler 406, and foot member 408. Transmission 404 may comprise first intermediate stage 410, which transmits a first intermediate torque about first intermediate axis 412, second intermediate stage 414, which transmits a second intermediate torque about second intermediate axis 416, third intermediate stage 418, which transmits a third intermediate torque about third intermediate axis 420, and final stage 422, which transmits a final torque about joint axis 424. The direction vector of each intermediate axis 412, 416, and 420 may be approximately perpendicular to the direction vector of joint axis 424.

As noted above, transmission 404 may comprise one or more types of transmission stages to obtain a desired torque and/or rotational speed about joint axis 424. For example, first intermediate stage 410 may be an epicyclic stage with a planetary configuration similar to and comprising the same elements as first intermediate stage 318 discussed with respect to FIG. 3. Final stage 422 may comprise hypoid pinion 426 and segmented hypoid ring gear 428, which may be similar to hypoid pinion 342 and segmented hypoid ring gear 344 discussed with respect to final stage 322 in FIG. 3. In contrast to the variation of transmission shown in FIG. 3, transmission 404 may comprise two intermediate stages between first intermediate stage 410 and final stage 422, second intermediate stage 416 and third intermediate stage 418, and four transmission stages total. Second intermediate stage 416 may comprise gear 430 and gear 432, the input and the output of second intermediate stage 416, respectively. Third intermediate stage 418 may comprise gear 432 and gear 434, the input and output of third intermediate stage 418, respectively. Thus, gear 432 may be the output of second intermediate stage 416 and the input of third intermediate stage 418. Each of gears 430, 432, and 434 may be any suitable type of gear, including but not limited to spur gears, helical gears, herringbone gears, or the like.

FIG. 5 is a schematic depiction of a side view of a variation of a lower limb prosthesis comprising a transmission with a looped transmission element. As shown, lower limb prosthesis 500 may comprise actuator 502, transmission 504, foot coupler 506, and foot member 508. Transmission 504 may comprise first intermediate stage 510, which transmits a first intermediate torque about first intermediate axis 512, second intermediate stage 514, which transmits a second intermediate torque about second intermediate axis 516, and final stage 518, which transmits a final torque about joint axis 520. First intermediate stage 510 may be an epicyclic stage with a planetary configuration, similar to and comprising the same elements as first intermediate stages 318 and 410 discussed with respect to FIGS. 3 and 4, respectively. Final stage 518 may be a hypoid stage comprising hypoid pinion 522 and segmented hypoid ring gear 524, and this hypoid stage may have a similar configuration and function as final stages 322 and 422 discussed with respect to FIGS. 3 and 4, respectively.

Second intermediate stage 514 may comprise wheels 526 and 528 and looped transmission element 530. Wheel 526 may be the input of second intermediate stage 514, and may receive the first intermediate torque from first intermediate stage 510. Rotation of wheel 526 may rotate looped transmission element 530, which may in turn rotate wheel 528. Wheel 528 may be the output of second intermediate stage 514, and may transmit the second intermediate torque to final stage 518. Wheels 526 and 528 may be any type of pulley or sprocket. Looped transmission element 530 may be a cable, belt (e.g., a ribbed belt, grooved belt, flat belt, or the like), or chain. In some variations, second intermediate stage 514 may comprise a tensioning mechanism (not shown) to maintain a tension in looped transmission element 530.

Figure 6A:
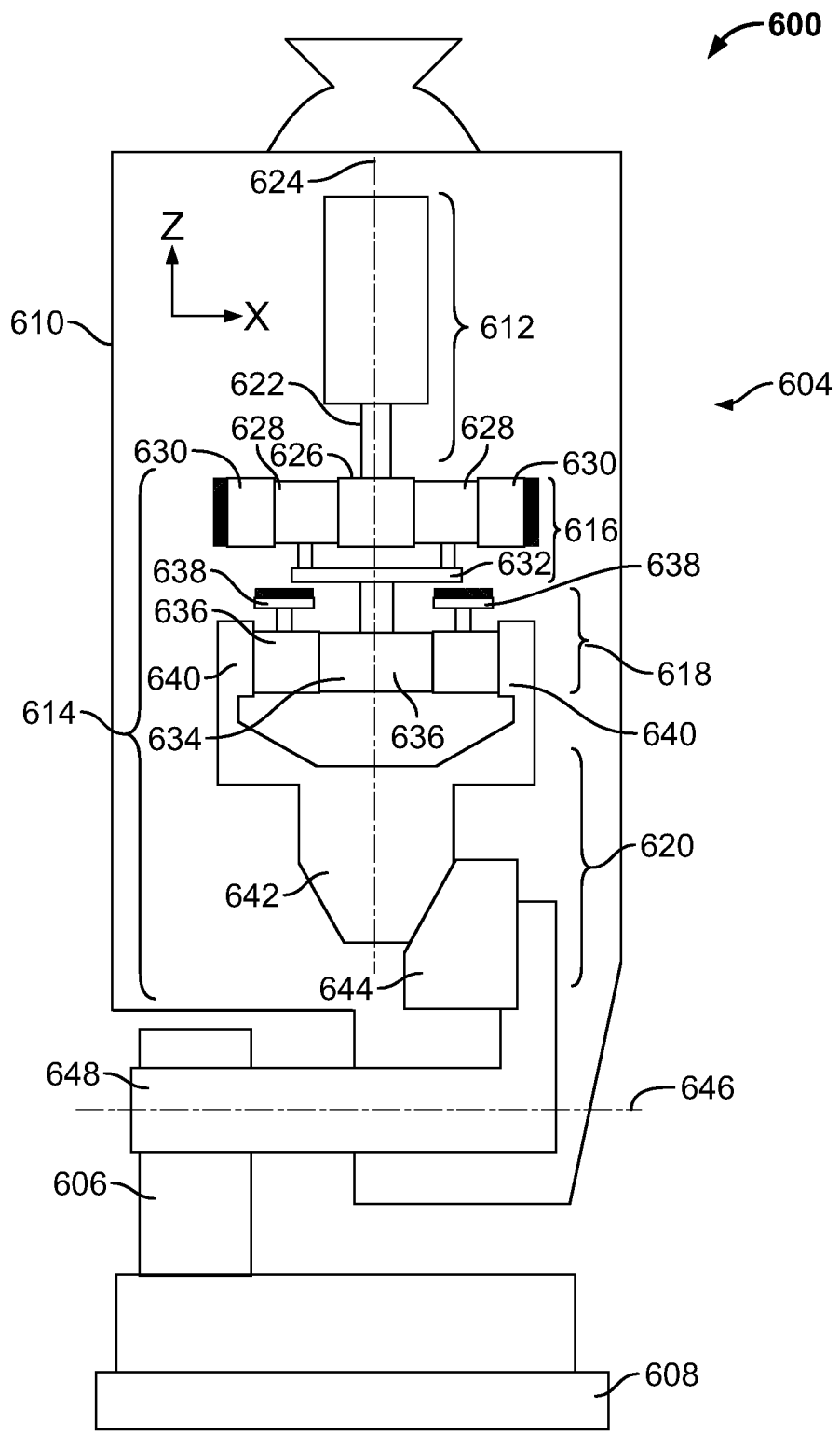
FIG. 6A is schematic representation of a variation of a lower limb prosthesis comprising a transmission with two epicyclic stages.

FIG. 6A is schematic representation of a variation of a lower limb prosthesis comprising a transmission with two epicyclic stages. As shown, lower limb prosthesis 600 may comprise main body 604, foot coupler 606, and foot member 608. Main body 604 may comprise housing 610, actuator 612, and transmission 614. Transmission 614 may comprise first intermediate stage 616, second intermediate stage 618, and final stage 620. As described with respect to other variations of lower limb prostheses, actuator 612 and each stage of transmission 614 may transmit a torque about an axis of rotation. However, in contrast to previously described variations, axis of rotation 624 may be the axis of rotation of actuator 612 (e.g., the axis of rotation of actuator shaft 622, which may be coupled to or integrally formed with a rotor of actuator 612), first intermediate stage 616, and second intermediate stage 618. In some instances, it may be advantageous for two or more axes of rotation (e.g., the axis of rotation of the actuator, the axis of rotation of the input and/or output of a transmission stage, and/or a joint axis) to be the same axis or aligned as this may allow for the volume occupied by the elements of main body 604 to be minimized and/or for the elements of main body 604 to occupy a desired overall shape or profile (e.g., a profile similar to a natural human shank).

In some embodiments, first intermediate stage 616 and second intermediate stage 618 may both be epicyclic stages, but they may have different configurations. The configuration of an epicyclic stage (e.g., planetary, star, solar) may determine which elements of the stage (e.g., sun gear, planet gear, carrier, annular gear) may rotate or orbit and which elements may be fixed. The configuration of an epicyclic stage may also determine which element is the input of the stage and which element is the output of the stage. As shown in FIG. 6, first intermediate stage 616 may have a planetary configuration, similar to first intermediate stage 318 discussed with respect to FIG. 3, and second intermediate stage 618 may have a star configuration. However, first intermediate stage 616 and second intermediate stage 618 may have any suitable combination of different epicyclic gear configurations or they may have the same configuration.

As discussed above with respect to first intermediate stage 318 in FIG. 3, first intermediate stage 616 of the embodiment shown in FIG. 6 may comprise sun gear 626, one or more planet gears 628, and annular gear 630 that is fixed relative main body 604. Sun gear 626 may be the input of first intermediate stage 616, and it may be coupled to actuator shaft 622 in order to receive an actuator torque. The actuator torque may result in rotation of sun gear 626, which may in turn rotate one or more planet gears 628 around sun gear 626 and within annular gear 630. One or more planet gears 628 may be coupled to carrier 632, and carrier 632 may be the output of first intermediate stage 616, transmitting a first intermediate torque to second intermediate stage 618.

As mentioned above, second intermediate stage 618 may be an epicyclic stage with a star configuration and may comprise sun gear 634, one or more planet gears 636 attached to carrier 638, and annular gear 640. Sun gear 634 may be the input of second intermediate stage 618, configured to receive the first intermediate torque. Sun gear 634 may rotate in response to the first intermediate torque, and in turn cause one or more planet gears 636 to rotate. However, in the star configuration, as opposed to the planetary configuration previously described, carrier 638 may be fixed relative to main body 604, and thus one or more planet gears 636 that are coupled to carrier 638 may rotate in place and not orbit around sun gear 634. Rotation of one or more planet gears 636 may rotate annular gear 640 about axis of rotation 624. Annular gear 640 may be the output of second intermediate stage 618 and transmit a second intermediate torque to final stage 620.

Final stage 620 may be a hypoid stage comprising hypoid pinion 642 and segmented hypoid ring gear 644. Hypoid pinion 642 may be coupled to or integrally formed with annular gear 640. For example, gear teeth of annular gear 640 may be cut or otherwise formed directly in hypoid pinion 642. Hypoid pinion 642 may be the input of final stage 620 and rotate about axis of rotation 624 in response to the second intermediate torque. Rotation of hypoid pinion 642 may result in rotation of segmented hypoid ring gear 644 about joint axis 646. Segmented hypoid ring gear 644 may be coupled to or integrally formed with output shaft 648, which may apply a final torque to foot member 608 via foot coupler 606.

Figure 6B:
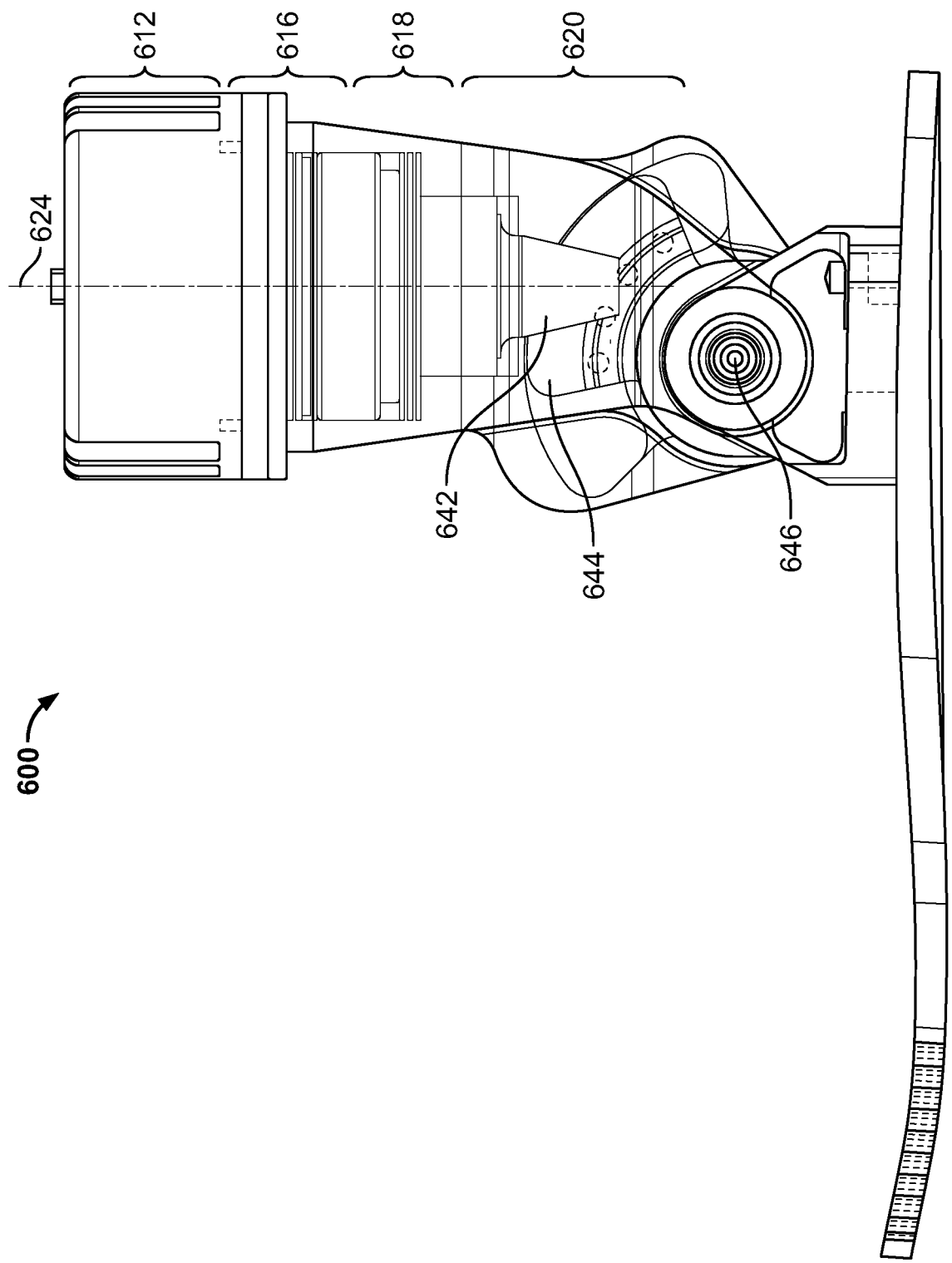
FIGS. 6B and 6C are side and cross-sectional views, respectively, of the lower limb prosthesis variation shown in FIG. 6A.
Figure 6C:
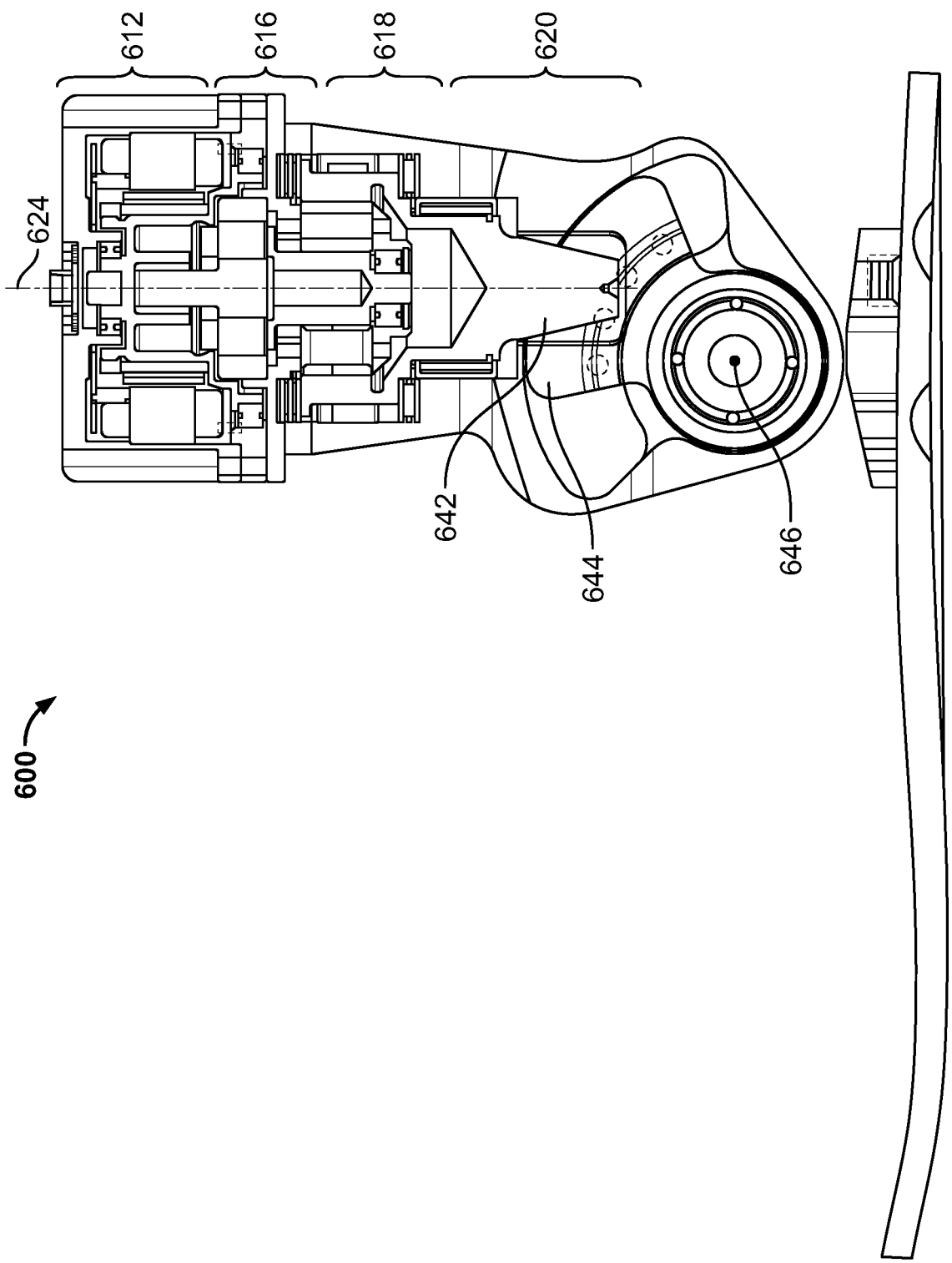

FIGS. 6B and 6C are side and cross-sectional views, respectively, of lower limb prosthesis 600 shown in FIG. 6A, and they further illustrate positional relationships between various elements of lower limb prosthesis 600. For example, actuator 612, first intermediate stage 616, and second intermediate stage 618 may be aligned such that axis of rotation 624 may be the axis of rotation of the actuator output and the inputs and outputs of the intermediate transmission stages. In some instances, axis of rotation 624 may be in the same plane as joint axis 646, while in other instances, as shown, axis of rotation 624 and joint axis 646 may be in different planes. In either case, the direction vector of axis of rotation 624 may be approximately perpendicular to the direction vector of joint axis 646. Thus, final stage 620 may change the orientation of the axis of rotation between the input of final stage 620, hypoid pinion 642, and the output of final stage 620, segmented hypoid ring gear 644. As mentioned, a transmission stage may change the orientation of an output axis of rotation relative to an input axis of rotation in one or more ways (e.g., change the orientation of the direction vector of an axis of rotation, shift the axis of rotation to a different plane, or the like).

Figure 7A:
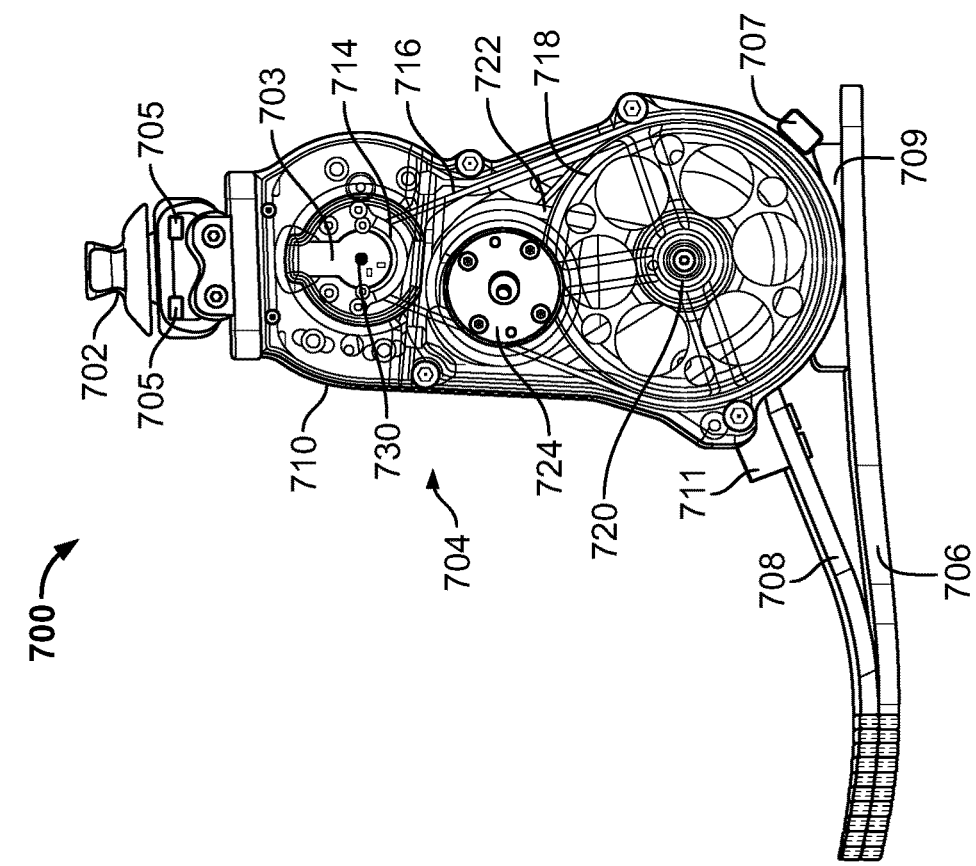
FIGS. 7A and 7B are side views of a variation of a lower limb prosthesis.
Figure 7B:
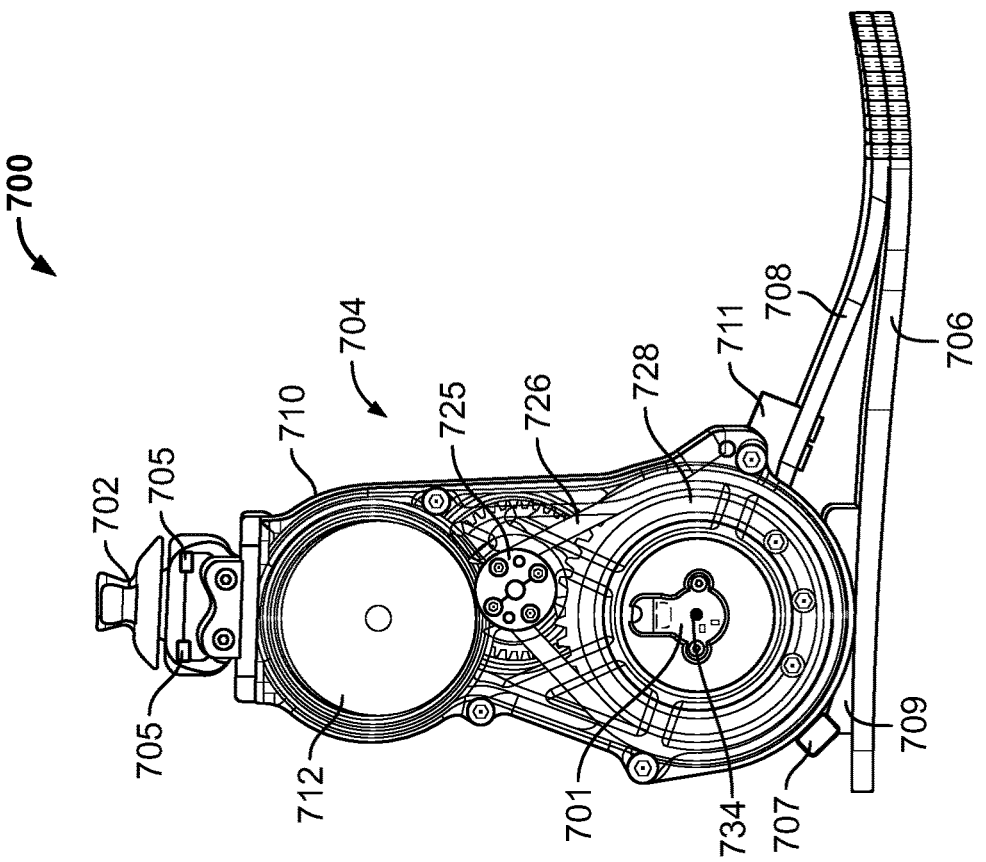
Figure 7C:
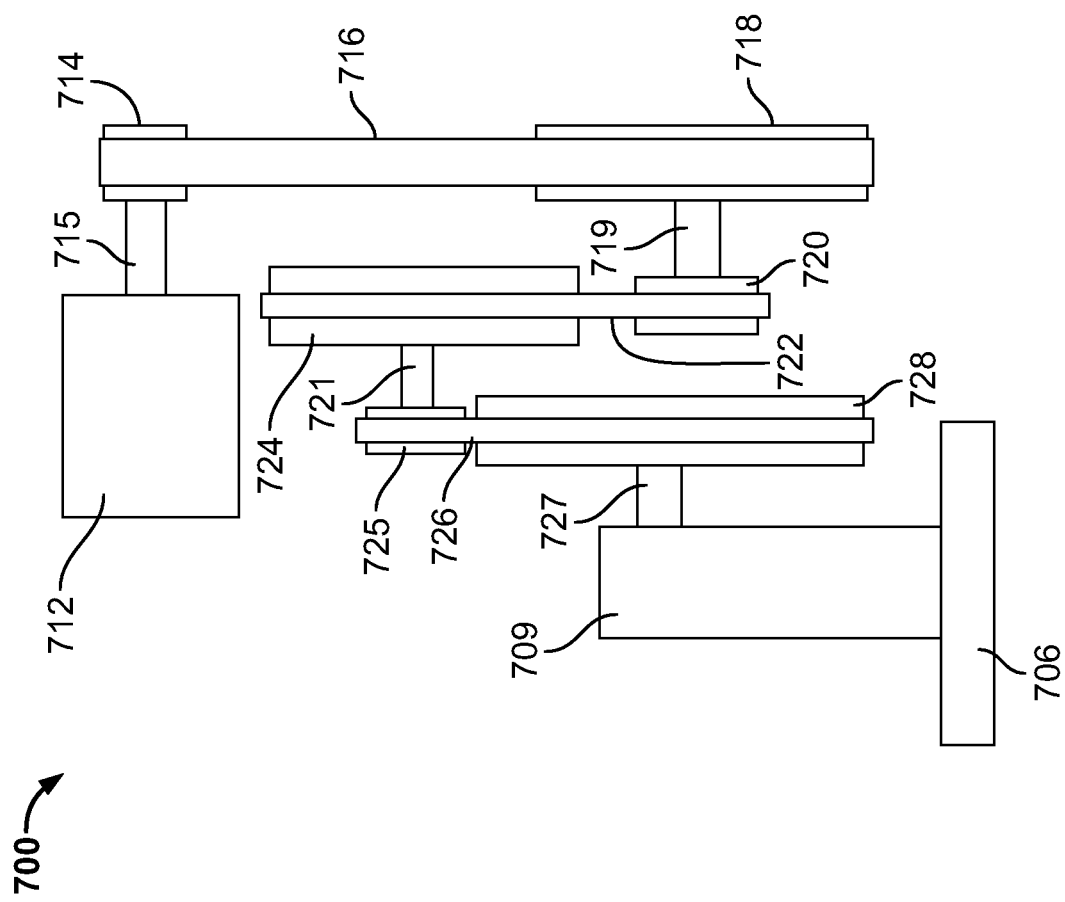
FIG. 7C is a schematic representation of the actuator and transmission of the lower limb prosthesis variation shown in FIGS. 7A and 7B.
Figure 7E:
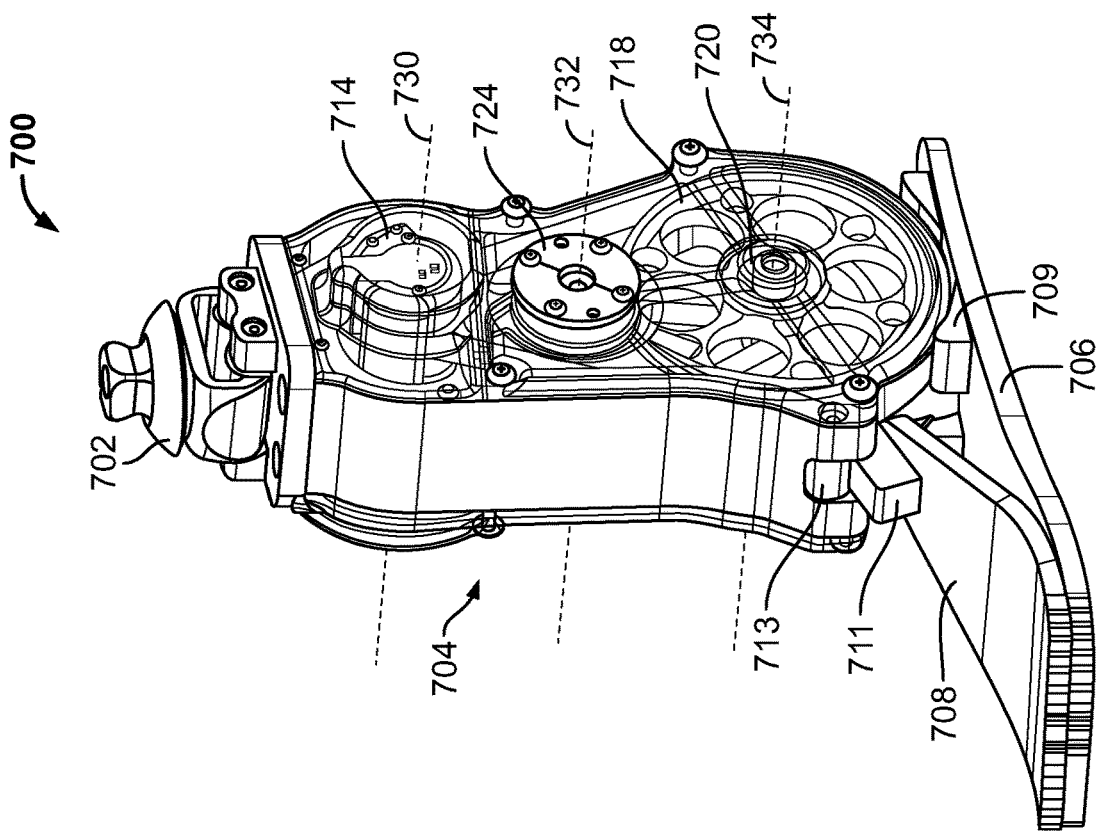
FIGS. 7D and 7E are isometric views of the lower limb prosthesis variation shown in FIGS. 7A-7C.
Figure 7D:
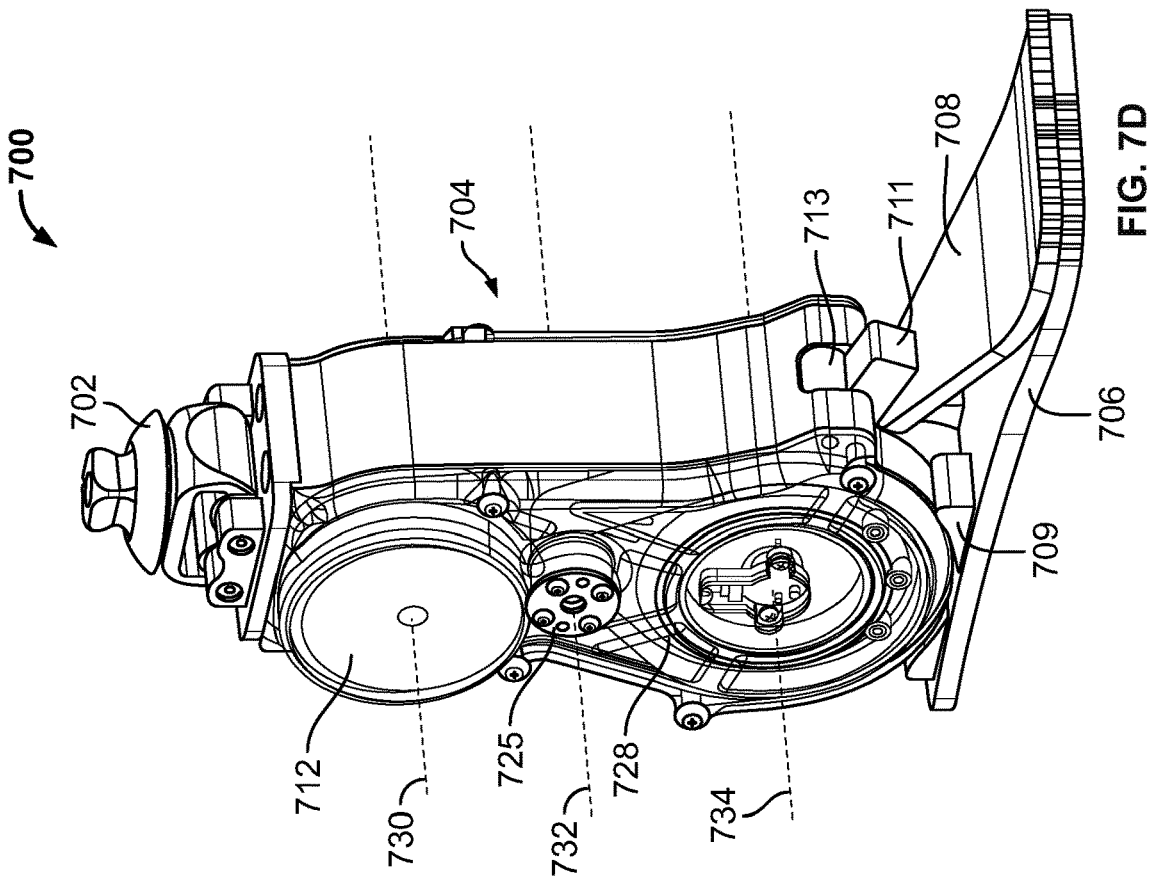

FIGS. 7A-7E are various views of a variation of a lower limb prosthesis comprising more than one looped element. In contrast to the variations of lower limb prostheses previously described, the axes of rotation of the actuator shaft and the transmission elements of the embodiment shown in FIGS. 7A-7E may have direction vectors that are parallel to the direction vector of the joint axis. FIGS. 7A and 7B are side views of right and left sides, respectively, of lower limb prosthesis 700, FIG. 7C is a schematic depiction of actuator 712 and the transmission of lower limb prosthesis 700, and FIGS. 7D and 7E are isometric views of right and left sides, respectively, of lower limb prosthesis 700.

Lower limb prosthesis 700 may comprise pyramid 702, main body 704, foot member 706, and foot coupler 709. Lower limb prosthesis 700 may also comprise several elements that will be described in more detail below, including spring 708, contact 711, engagement mechanism 713 (depicted in FIGS. 7E and 7F), and sensors 701, 703, 705, and 707 (depicted in FIGS. 7A and 7B). Main body 704 of lower limb prosthesis 700 may comprise housing 710, actuator 712, and multiple transmission elements.

As seen best in FIG. 7C, actuator 712 may transmit an actuator torque to a first intermediate stage via actuator shaft 715. The first intermediate stage may comprise wheel 714, looped element 716, and wheel 718. Wheel 714 may be the input of the first intermediate stage, and it may rotate in response to the actuator torque. Rotation of wheel 714 may rotate looped element 716, which may in turn rotate wheel 718, the output of the first intermediate stage. Wheel 718 may apply a first intermediate torque via shaft 719 to wheel 720, which may be the input of the second intermediate stage. The second intermediate stage may comprise wheel 720, looped element 722, and wheel 724, and rotation of wheel 720 may result in rotation of looped element 722 and wheel 724. Wheel 724 may be the output of the second intermediate stage, and it may apply a second intermediate torque via shaft 721 to the input of the final stage, wheel 725. The final stage may comprise wheel 725, looped element 726, and wheel 728. Rotation of wheel 725 may rotate looped element 726, thereby rotating wheel 728. Wheel 728 may be the output of the final stage, and it may be directly or indirectly coupled to foot member 706 such that rotation of wheel 728 may result in rotation of foot member 706. As shown, wheel 728 may be coupled to foot member 706 via output shaft 727 of the transmission and foot coupler 709.

Each of wheels 714, 718, 720, 724, and 728 may be any suitable rotational element configured to transmit a torque to a looped element, for example, a sprocket, a pulley, or the like. Each of looped elements 716, 722, and 726 may be any loop element configured to transmit a torque from one wheel to another wheel, for example, a chain, cable, belt (e.g., a ribbed belt, grooved belt, flat belt, or the like), or the like. In some variations, a looped element may be configured to function with or may correspond to a particular type of wheel and vice versa. For example, in some instances, the looped element may comprise a chain and the wheel may comprise a sprocket, while in other variations the looped element may comprise a belt and the wheel may comprise a pulley. It should be appreciated that any combination of looped elements and wheels that are configured to work together may be used. In the embodiment shown in FIGS. 7A-7E, wheels 714 and 718 may be pulleys, wheels 720, 724, and 728 may be sprockets, looped element 716 may be a belt, and looped elements 722 and 726 may be chains. However, other variations may comprise different arrangements of wheel types and corresponding looped elements (e.g., wheels 714 and 718 may be sprockets and looped element 716 may be a chain). As noted above, providing at least two intermediate transmission stages may be advantageous because doing so may allow for more precise control of an angular velocity of foot member 706 relative to main body 704 and of a torque applied to foot member 706.

As mentioned previously, the actuator and each transmission stage of the lower limb prostheses described here may each transmit torque about an axis of rotation. In the variation of a lower limb prosthesis shown in FIGS. 7A-7E, the axes of rotation of actuator 712 and of each transmission stage may be orientated similarly. More specifically, the axes of rotation of actuator 112, the first intermediate stage, the second intermediate stage, and the final stage may have direction vectors that are parallel to each other and to the joint axis. The axes of rotation of lower limb prosthesis 700 may be seen best in FIGS. 7D and 7E. Actuator 712 and wheel 714 may have axis of rotation 730, wheels 724 and 725 may have axis of rotation 732, and wheels 718, 720, and 728 may have axis of rotation 734. Since rotation of wheel 728 may cause rotation of foot member 706 relative to main body 704, axis of rotation 734 may also be the joint axis. In contrast to the variations of lower limb prostheses discussed with respect to FIGS. 3-6, the direction vectors of axes of rotation 730, 732, and 734 of lower limb prosthesis 700 may be parallel to the direction vector of the joint axis. This configuration may be less mechanically complicated than variations of lower limb prostheses that comprise one or more transmission stages with direction vectors that are perpendicular to the direction vector of the joint axis.

Controller and Sensors

The lower limb prostheses described here may comprise a control system comprising a controller and one or more sensors configured to provide prosthetic information to the controller. In some variations, the controller may comprise a processor and memory, and it may be configured to control one or more operations of the lower limb prosthesis. For example, the controller may be configured to control a torque produced by an actuator by providing a torque command to the actuator. The torque command may be determined by a control algorithm stored in the memory of the controller and/or generated in response to prosthetic information (e.g., information indicating a velocity, torque, position, orientation, or the like of the lower limb prosthesis) detected by one or more sensors. In some variations, as will be described in detail herein, the controller may be configured to control a position and/or function of a spring of the lower limb prosthesis. The controller and other elements of the lower limb prosthesis, such as the actuator, may be powered by a battery or other power source.

The lower limb prosthesis may comprise one or more sensors to detect information about the prosthesis, and this prosthetic information may be delivered to the controller. The one or more sensors may include one or more sensor types, including but not limited to force sensors (e.g., load cells, piezoelectric force sensors, strain gauges, and the like), absolute encoders, incremental encoders, inertial measurement units (IMUs), position sensors, hall sensors, and/or the like. The type of sensor and the position of a sensor relative to other elements of the lower limb prosthesis may determine, at least in part, the type of signal detected by the sensor and the way in which the signal is used or processed by the controller. For example, an absolute and/or incremental encoder may be positioned on the actuator or transmission to detect position and/or angular velocity information of a shaft, gear, or other element of the actuator or transmission. This information may be delivered to the controller, and the controller may adjust the torque command delivered to the actuator based on this information.

Figure 8:
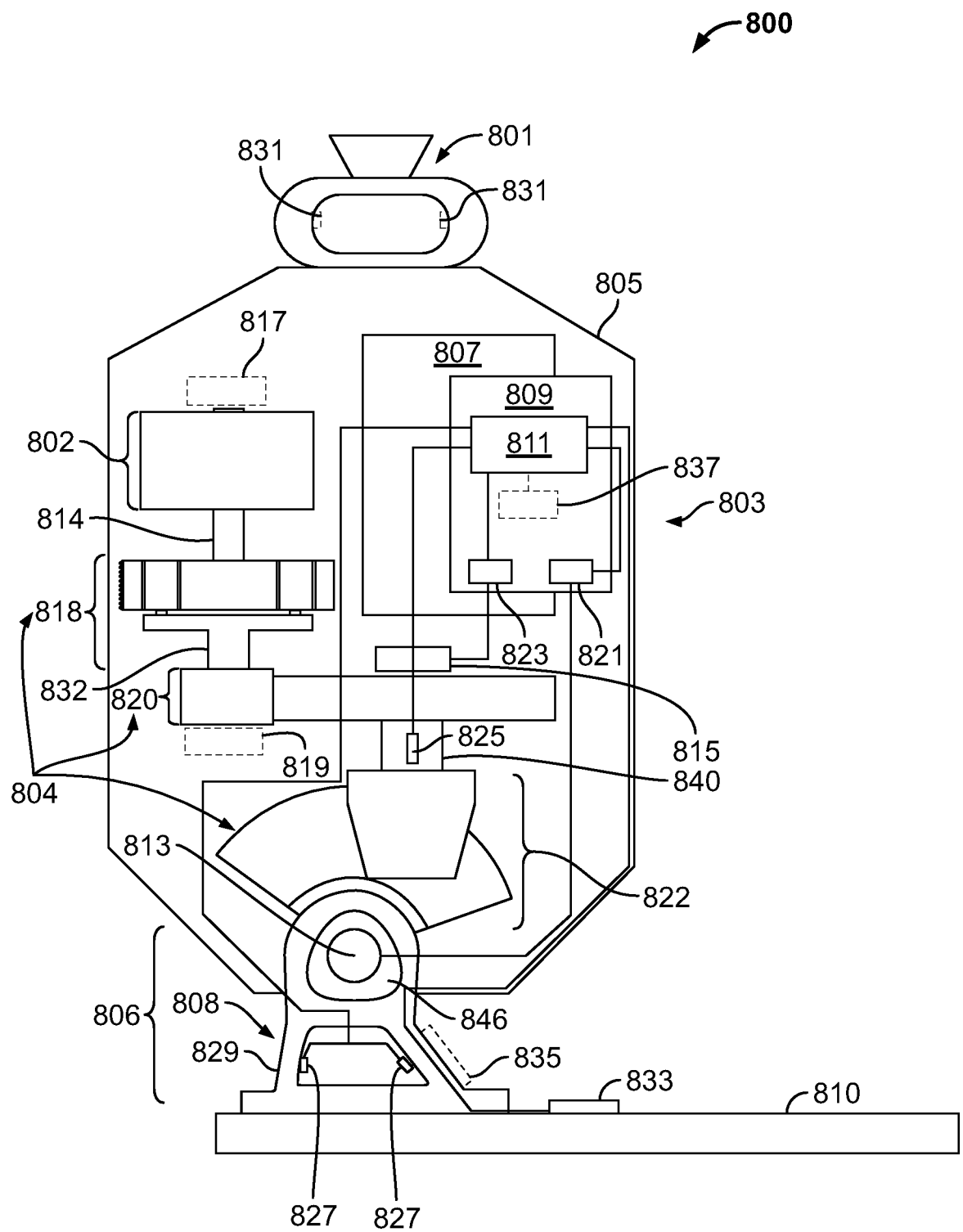
FIG. 8 is a schematic representation of a variation of a lower limb prosthesis that depicts possible positions of a controller and sensors.

FIG. 8 is a schematic depiction of a variation of a lower limb prosthesis depicting possible locations for a power source and a controller relative to other elements of the lower limb prosthesis. Lower limb prosthesis 800 may comprise pyramid 801, main body 803, foot coupler 808, and foot member 810. Main body 803 may comprise housing 805, actuator 802, and transmission 804. Actuator 802 and transmission 804 may be similar to and comprise the same elements as actuator 302 and transmission 304, discussed with respect to lower limb prosthesis 300 in FIG. 3, with like elements labeled similarly. In addition, lower limb prosthesis 800 may comprise battery 807 and circuit board 809 with controller 811. As shown, battery 807 and/or circuit board 809 with controller 811 may be positioned laterally adjacent to first intermediate stage 818 and vertically adjacent to second intermediate stage 820. In some variations, it may be desirable to position battery 807 and/or circuit board 809 in a space adjacent to a transmission stage because this may utilize space efficiently within main body 803, which may allow lower limb prosthesis 800 to have a smaller volume and/or occupy an anatomical envelope of a natural leg. Although depicted within housing 805, in some variations, battery 807, circuit board 809, circuitry, and/or any other element of lower prosthesis 800 may be positioned at least partially external to housing 805. For example, in some variations, battery 807 may be coupled to an external surface of housing 805, foot coupler 808 or foot member 810. Battery 807 may be wired or wirelessly connected to one or more elements (e.g., controller, actuator) within housing 805.

In some variations, battery 807 may comprise a rechargeable battery such as a lithium ion battery, which may power actuator 802, controller 811, and/or circuitry of lower limb prosthesis 800. In these variations, battery 807 may be charged by wires or wirelessly (e.g., through inductive charging). However, any power source may be used with lower limb prosthesis 800 that has a suitable voltage.

Controller 811 may comprise one or more processors such as a microcontroller, a DSP, an ASIC, an FPGA, hard-wired logic, analog circuitry, the like, and/or a combination thereof. Controller 811 may comprise a memory (e.g., a flash memory) for storing computer-executable instructions that are executed by one or more processors of controller 811. In some variations, controller 811 may comprise a system on a chip (SoC).

FIG. 8 also illustrates possible positions of various types of sensors on lower limb prosthesis 800. For example, lower limb prosthesis 800 may comprise absolute encoder 813, which may be configured to provide a position signal to controller 811 indicating an angular position of foot member 810 relative to main body 803. In some variations, at least a portion of absolute encoder 813 may be positioned on a portion of joint 806, such as output shaft 846 of transmission 804. Absolute encoder 813 may comprise, for example, a magnetic encoder, an optical encoder, a mechanical or contact encoder, a capacitive encoder, or the like. In some variations, absolute encoder 813 may comprise a permanent magnet mounted on a portion of joint 806 and a magnetic sensor in close proximity to the permanent magnet. The magnetic sensor may be configured to detect an angular position of the permanent magnet. Absolute encoder 813 may then provide a position signal to controller 811 indicating the angular position of the permanent magnet, which may also indicate the angular position of foot member 810 relative to main body 803.

In some variations, lower limb prosthesis 800 may comprise incremental encoder 815, which may be configured to provide an incremental signal to controller 811 indicating a change in an angular position. As shown in FIG. 8, incremental encoder 815 may be located in the vicinity of or on shaft 840 of transmission 804, and incremental encoder 815 may be configured to detect changes in an angular position of shaft 840. Additionally or alternatively, an incremental encoder may be positioned at other locations, such as other locations on transmission 804 and/or on actuator 802. For example, an incremental encoder may be positioned at location 817, in the vicinity of or on actuator shaft 814, and/or at location 819, in the vicinity of or on the output of first intermediate stage 818, here, carrier 832. Incremental encoder 815 may comprise, for example, a magnetic encoder, mechanical encoder, optical encoder, or the like.

As shown in FIG. 8, absolute encoder 813 may be electronically connected to controller 811 through filter 821, which may comprise, for example, a low pass filter to attenuate frequencies above a threshold frequency that may comprise noise in the position signal. Incremental encoder 815 may be electronically connected to controller 811 through filter 823, which may comprise, for example, a high pass filter to attenuate frequencies below a threshold frequency that may comprise noise in the incremental signal. In other variations, filter 821 may comprise a high pass filter and/or filter 823 may comprise a low pass filter.

In some variations, controller 811 may be configured to use the position signal provided by absolute encoder 813 and/or the incremental signal provided by incremental encoder 815 to determine an angular position of foot member 810 relative to main body 803. Additionally or alternatively, controller 811 may use the position signal and/or the incremental signal to determine an angular velocity or acceleration of foot member 810 relative to main body 803. In some instances, using both the position signal and the incremental signal may provide more accurate measurements of the angular position and/or the angular velocity of foot member 810 relative to main body 803 than if a single signal was used. It should be appreciated that the angular position and/or angular velocity of foot member 810 relative to main body 803 may be determined directly or indirectly. For example, an absolute encoder and/or an incremental encoder may detect an angular position and/or velocity of an element or elements other than foot member 810 and/or main body 803, such as the angular position and/or velocity of a portion of actuator 802 and/or transmission 804. The prosthetic information obtained in these variations may be used by the controller to indirectly determine the angular position and/or velocity of foot member 810 relative to main body 803.

In some variations, lower limb prosthesis 800 may comprise one or more torque sensors, force sensors, and/or combination torque and force sensors. The location of a torque and/or force sensor may determine, at least in part, the torque and/or force that are detected. For example, lower limb prosthesis 800 may comprise one or more torque sensors positioned on transmission 804, such as torque sensor 825, which may be positioned on shaft 840. Torque sensor 825 may comprise, for example, a set of strain gauges that detect strains on shaft 840. Shaft 840 may transmit an intermediate torque to final stage 822 of transmission 804, and torque sensor 825 may provide a torque signal to controller 811 that indicates the intermediate torque. Controller 811 may use the torque signal to adjust the torque command communicated to actuator 802 in order to adjust the torque produced by actuator 802. By measuring an intermediate torque of transmission 804, controller 811 may control actuator 802 more precisely.

In some variations, one or more torque and/or force sensors may be positioned on foot coupler 808. For example, sensor 827 may be a torque and/or force sensor. Sensor 827 may be electronically connected to controller 811 and may comprise, for example, one or more strain gauges mounted on foot coupler 808. In some variations, sensor 827 may comprise one or more strain gauges mounted on one or more structural beams 829 of foot coupler 808. For example, one or more strain gauges may be mounted on every structural beam 829 (e.g., one strain gauge on each of 4 total structural beams 829), or one or more strain gauges may be mounted on only some structural beams 829 of foot coupler 808 (e.g., on one beam, two beams, or three beams). Deformation or strain in structural beams 829 may be detected by sensor 827, which may then provide a torque and/or force signal to controller 811 that may indicate a torque and/or force between main body 803 and foot member 810. Controller 811 may use the torque and/or force signal to determine a particular torque command to deliver to actuator 802 that may result in actuator 802 and transmission 804 generating a particular torque between main body 803 and foot member 810. Controller 811 may additionally or alternatively use the torque and/or force signal provided by sensor 827 to determine a particular phase of gait or a motion of a user. In some variations, it may be desirable to position sensor 827 on foot coupler 808 or foot member 810 as compared to other locations on lower limb prosthesis 800 because doing so may provide more accurate measurements of forces applied to foot member 810, such as ground reaction forces and/or a torque applied by final stage 822 of transmission 804.

In some variations, lower limb prosthesis 800 may comprise torque and/or force sensors 831 mounted on pyramid 801. Torque and/or force sensors 831 may be in addition to or in place of other torque and/or force sensors on lower limb prosthesis 800 (e.g., sensor 827). In some variations, torque and/or force sensors 831, which may be located on structural beams of pyramid 801, may be configured to detect a strain or deformation of pyramid 801 and provide a torque and/or force signal to controller 811. Controller 811 may use the torque and/or force signal from torque and/or force sensors 831 to determine a torque and/or a force between pyramid 801 and main body 803. Additionally or alternatively, controller 811 may use the torque and/or force signal from torque and/or force sensors 831 to estimate a ground reaction force and/or the final torque applied by transmission 804.

While not shown in FIG. 8, it should be appreciated that a torque and/or force sensor may be positioned at locations other than transmission 804, foot coupler 808, or pyramid 801. For example, one or more torque and/or force sensors may be positioned on or integrated into any suitable structure of main body 803. For example, in some variations, one or more torque and/or force sensors maybe integrated into housing 805 of main body 803 (e.g., coupled to an internal or external surface of housing 805 and/or embedded within a thickness of housing 805). Additionally or alternatively, one or more torque and/or force sensors may be positioned on or integrated into a structure of foot member 810.

In some variations, lower limb prosthesis 800 may comprise one or more IMUs, and each IMU may comprise one or more gyroscopes and/or accelerometers. An IMU may be configured to provide a signal to controller 811 indicating at least one of a velocity, acceleration, or orientation of at least a portion of lower limb prosthesis 800. In some variations, lower limb prosthesis 800 may an IMU positioned on foot member 810 and/or an IMU positioned at on foot coupler 808. For example, an IMU may be positioned on an external surface of foot member 810, such as IMU 833 that may be on an external dorsal surface of foot member 810, and/or an IMU may be integrated into the thickness of foot member 810. Similarly, an IMU may be positioned on an external surface of foot coupler 808, such as at location 835 on an external surface of structural beam 829, and/or an IMU may be integrated into the thickness of foot coupler 808. Compared to other locations on lower limb prosthesis 800, it may be advantageous to position an IMU on foot member 810 or on foot coupler 808, as this may allow the IMU to provide a signal that more accurately indicates an orientation, velocity, and/or acceleration of foot member 810. For example, IMU 833 may provide a signal that indicates the pitch of foot member 810 (e.g., an angle of foot member 810 relative to flat ground, an angle between foot member 810 and main body 803). In some variations, an IMU may be positioned within housing 805 of main body 803, such as at location 837 on circuit board 809, which may allow for less wiring between the IMU and controller 811. In other variations, an IMU may be positioned on an external surface of housing 805.

In some variations, controller 811 may use one or more of the velocity, acceleration, and/or orientation signal provided by IMU 833 to determine a torque command to provide to actuator 802. For example, controller 811 may use one or more signals from IMU 833 to determine a torque command that may adjust the angular position of foot member 810 relative to main body 803 in order to accommodate for changes in the slope of the ground beneath foot member 810. This adjustment may be based on orientation information provided by IMU 833 while foot member 810 is on the ground, such as the pitch of foot member 810 mentioned above. In some variations, controller 811 may use a single formula to determine an adjustment for a slope regardless of whether the slope is greater or less than a predetermined angle. In other variations, controller 811 may determine an adjustment for a slope using multiple formulas. Additionally or alternatively, as will be discussed in detail herein, controller 811 may adjust a position of a spring (not shown) of lower limb prosthesis 800 in response to one or more signals provided by IMU 833.

Returning to FIGS. 7A and 7B, possible positions of various sensors are shown with respect to lower limb prosthesis 700, which illustrates that the sensors discussed with respect to FIG. 8 may be positioned on any of the lower limb prosthesis variations described herein. For example, lower limb prosthesis 700 may comprise absolute encoder 701, incremental encoder 703, torque and/or force sensors 705, and/or IMU 707. Absolute encoder 701 may be located at or near axis of rotation 734, which may be the joint axis. Absolute encoder 701 may be configured to provide a position signal to a controller (not shown) of lower limb prosthesis 700 indicating an angular position of foot member 706 relative to main body 704. Incremental encoder 703 may be located at or near wheel 714 and axis of rotation 730, and it may be configured to provide an incremental signal indicating a change in angular position of wheel 714. As discussed above with respect to FIG. 8, the position signal from absolute encoder 701 and the incremental signal from incremental encoder 703 may be used individually or together by a controller of lower limb prosthesis 700 to accurately determine an angular position and/or an angular velocity of foot member 706 relative to main body 704.

Lower limb prosthesis 700 may comprise one or more torque and/or force sensors such as torque and/or force sensors 705 positioned on pyramid 702. Torque and/or force sensors 705 may be configured to provide torque and/or force signals to indicate, for example, one or more forces and/or a torque between pyramid 702 and main body 704. Lower limb prosthesis 700 may additionally or alternatively comprise IMU 707, which may be positioned on foot coupler 709. IMU 707 may be configured to provide one or more signals indicating a velocity, an acceleration, and/or an orientation of at least a portion of lower limb prosthesis 700. For example, positioning IMU 707 on foot coupler 709 may facilitate accurate detection of a velocity, an acceleration, and/or an orientation of foot member 706 relative to main body 704.

The lower limb prostheses described here may comprise one or more sensors or sensor types not shown in FIG. 7A, 7B, or 8. For example, the lower limb prosthesis may comprise one or more Hall sensors. In some variations, an actuator of the lower limb prosthesis, such as a brushless DC motor, may comprise one or more Hall effect sensors to detect a rotor position relative to a stator and/or commutate the motor. As will be discussed in detail herein, some variations of lower limb prostheses may comprise a spring, and the position of the spring may be adjusted with an engagement mechanism. In some of these variations, the lower limb prostheses may comprise an engagement position sensor, which may be configured to provide a signal to a controller indicating a position of the spring. The engagement position sensor may comprise, for example, a position sensor such as a Hall effect sensor, an optical sensor, a contact sensor, or an inductive sensor.

Spring

In some variations, a lower limb prosthesis may comprise a spring that is coupled directly or indirectly to a foot member and a main body. The spring may be configured to act in parallel to a torque produced by an actuator and transmitted to the foot member through a transmission. In other words, the spring may exert a spring force on the foot member that may result in a torque about a joint axis. A final stage of the transmission may also apply a torque about the joint axis, and thus the torque produced as a result of the spring force and the torque transmitted by the transmission may be additive.

FIGS. 9A-9C depict a variation of a lower limb prosthesis comprising a spring under different conditions. As shown, lower limb prosthesis 900 may comprise main body 902, foot coupler 904, foot member 906, and spring 908. Spring 908 may be at least temporarily coupled to foot member 906, and in some variations spring 908 may be integrally formed with foot member 906. As shown, a distal end of spring 908 may be coupled to a distal toe portion of foot member 906. However, spring 908 may be coupled to one more locations between the distal toe portion and a proximal heel portion of foot member 906 (e.g., at a mid-point between foot coupler 904 and distal end 910, between the mid-point of foot member 906 and distal end 910, between the mid-point of foot member 906 and foot coupler 904).

In some variations, a spring may be engaged with a main body. The spring may be at least temporarily engaged with the main body through direct or indirect attachment, coupling, contact, or the like. The spring may be engaged with the main body at an engagement position, which may be a position of the spring (e.g., the position of a portion of the spring, the position of the proximal end of the spring) relative to the main body. In some variations, as will be described in detail herein, lower limb prostheses may be configured so that the engagement position may be adjusted (i.e., the position where the spring engages the main body may be adjusted), whereas in other variations the engagement position may be fixed. For example, returning to FIGS. 9A-9C, a proximal end of spring 908 may be engaged with main body 902 through engagement mechanism 912 and contact 914, which may be configured to adjust the engagement position of spring 908. In other variations, spring 908 may be engaged with main body 902 without the use of engagement mechanism 912 and/or contact 914, and the engagement position may be fixed.

While spring 908 is shown in FIGS. 9A-9C as a leaf spring, lower limb prosthesis 900 may additionally or alternatively comprise one or more other types of springs, including but not limited to a coil compression spring, a lever spring (e.g., a carbon fiber lever spring), an air piston or gas spring, or any other spring mechanism capable of storing a desired amount of energy. While one spring is shown in FIGS. 9A-9C, it should be appreciated that some variations of lower limb prostheses may comprise more than one spring (e.g., two, three, four, or more).

In some variations, a spring of a lower limb prosthesis may be moveable between an equilibrium state and a loaded state. When the spring is in an equilibrium state, or in equilibrium, it may not store or provide energy. When a sufficient force is applied to the spring, such as by rotation of the foot member relative to the main body, the spring may move from the equilibrium state to the loaded state, or become loaded. When the spring is loaded, it may store and provide energy. It should be appreciated that the spring may be in the loaded state when any energy is stored in the spring, and thus the degree of loading and the amount of energy stored in the spring may vary while the spring is in the loaded state. The spring may be biased toward the equilibrium state, and thus when the loaded spring is unconstrained, it may tend to return to equilibrium.

For example, FIG. 9A depicts spring 908 in equilibrium, or in an equilibrium state, and FIG. 9B depicts spring 908 loaded, or in a loaded state. As shown, when spring 908 is loaded it may deflect from its equilibrium position. However, in some variations, spring 908 may compress, contract, expand, or the like, when loaded. As mentioned, when spring 908 is in equilibrium, it may not store or provide energy, whereas when spring 908 is loaded, it may store and provide energy. Spring 908 may move between an equilibrium state and a loaded state when an angle and a distance between foot member 906 and main body 902 change, thereby causing a force to be applied to spring 908. For example, any dorsiflexion of foot member 906 from the position shown in FIG. 9A where spring 908 is in equilibrium, such as dorsiflexion to the position shown in FIG. 9B, may load spring 908 and cause it to store energy. Spring 908 may release the stored energy as a spring force applied to foot member 906 and main body 902, resulting in a torque about joint axis 916 that may cause plantar flexion of foot member 906. Additionally or alternatively, spring 908 may be configured to become loaded and store energy when foot member 906 is plantarflexed beyond the position when spring 908 is in equilibrium. In these variations, energy stored in spring 908 during the plantar flexion motion may be released as a spring force applied to foot member 906, resulting in a torque about joint axis 916 that may cause dorsiflexion of foot member 906.

As mentioned, the spring force applied by spring 908 may act in parallel to the torque produced by actuator 918 and applied by transmission 920 to foot member 906. In other words, the spring force and the final stage of transmission 920 may each cause a torque to be applied about joint axis 916, and these torques may be additive. An overall or total torque applied to foot member 906 may be the sum of the torque resulting from the spring force and the torque applied by the final stage of transmission 920. Thus, compared to variations of lower limb prostheses without spring 908, less torque may need to be produced by actuator 918 in order to apply the same overall torque about joint axis 916. This may allow actuator 918 to be smaller and/or use less power. In some variations, a lower power requirement for actuator 918 may allow a battery of lower limb prosthesis 900 to be smaller and/or have a longer use time between charges. Decreasing the size of actuator 918 and/or the battery may also allow the overall size and/or weight of main body 902 to be decreased. For a given actuator 918 and power source, the addition of spring 908 may also allow the overall torque applied to foot member 906 to be greater. In some variations, generating a greater overall torque may be advantageous because it may more effectively propel a heavier user during push off.

Engagement Mechanism

As mentioned, in some variations of a lower limb prosthesis, a spring may engage a main body through an engagement mechanism. In some of these variations, the spring and the engagement mechanism may be engaged or joined at a contact, which will be described in more detail herein. The engagement mechanism may be configured to adjust the function and/or position of the spring in one or more ways. For example, the engagement mechanism may engage and disengage the spring. In some variations, when the spring is engaged, or in an engaged state, a portion of the spring may be locked or fixed relative to the engagement mechanism. In the engaged state, changes in an angle between the foot member and the main body may result in changes in an amount of energy stored in the spring. In other words, when the spring is in the engaged state, the spring may be configured to be loaded and to apply a spring force to the foot member. When the spring is disengaged, or in the disengaged state, changes in an angle between the main body and the foot member may not result in substantial changes to an amount of energy stored in the spring, and the spring may remain in equilibrium. In other words, when the spring is disengaged, it may be configured not to apply a spring force to the foot member.

FIGS. 9A-9C demonstrate differences between the engaged state and the disengaged state of a spring. In FIGS. 9A and 9B, spring 908 may be engaged with engagement mechanism 912 (i.e., spring 908 may be engaged, engagement mechanism 912 may be engaged). As the angle between main body 902 and foot member 906 decreases from FIG. 9A to FIG. 9B, spring 908 may be loaded, store energy, and apply a spring force to foot member 906. In contrast, FIG. 9C depicts lower limb prosthesis 900 with spring 908 in a disengaged state. When spring 908 is disengaged, the angle between main body 902 and foot member 906 may change without spring 908 being loaded. Thus, while FIGS. 9B and 9C both show foot member 906 in a dorsiflexed position, engaged spring 908 in FIG. 9B may be loaded and may store energy, whereas disengaged spring 908 in FIG. 9C may be in equilibrium.

FIGS. 10A-10K depict another variation of a lower limb prosthesis in various positions, and these figures also illustrate the concepts of spring engagement and disengagement. As shown, lower limb prosthesis 1000 may comprise main body 1002, foot member 1004, spring 1006, and engagement mechanism 1008. Engagement mechanism 1008 may comprise piston 1010 slidably disposed in chamber 1012, and piston 1010 may be coupled to spring 1006 via piston rod 1014 and contact 1016. A variation of an engagement mechanism similar to engagement mechanism 1008 will be described in detail with respect to FIGS. 14A-14C.

FIGS. 10A and 10B depict lower limb prosthesis 1000 with spring 1006 engaged with engagement mechanism 1008. In FIG. 10A, spring 1006 may be in equilibrium. However, as shown in FIG. 10B, when foot member 1004 is dorsiflexed (i.e., an angle between foot member 1004 and main body 1003 decreases), spring 1006 may be loaded, store energy, and apply a spring force. When spring 1006 is engaged, piston 1010 may remain substantially fixed relative to chamber 1012.

FIGS. 10C-10E depict lower limb prosthesis 1000 with spring 1006 disengaged from engagement mechanism 1008. As shown in FIG. 10C, spring 1006 may be in equilibrium when foot member 1004 is approximately perpendicular to main body 1002. With spring 1006 disengaged, foot member 1004 may be dorsiflexed or plantarflexed, as shown in FIGS. 10D and 10E, respectively, without changes in the loading or energy storage of spring 1006. Despite the fact that foot member 1004 has different angular positions relative to main body 1002 in FIGS. 10C-10E, because spring 1006 is disengaged, spring 1006 may remain in equilibrium in each of these positions. In order for spring 1006 to remain in equilibrium during dorsiflexion and plantar flexion, piston 1010 may slide within chamber 1012 when spring 1006 is disengaged. Thus, piston 1010 is shown in different positions relative to chamber 1012 and main body 1002 in FIGS. 10C-10E. As spring 1006 is coupled to piston 1010, changing the position of piston 1010 relative to main body 1002 may also change the position of spring 1006 relative to main body 1002.

A lower limb prosthesis may be configured to engage and disengage a spring at specific times. For example, it may be advantageous for an engagement mechanism to disengage the spring when the spring has been loaded for a prolonged, predetermined period of time. This situation may occur, for example, if the spring is engaged and a user is standing still on a sloped ground, or the user is sitting with a foot member of the lower limb prosthesis dorsiflexed or plantar flexed. If the foot member is held in a dorsiflexed or plantar flexed position while the spring is loaded, a user may experience a constant spring force acting to plantarflex or dorsiflex the foot member, respectively, in order to return the spring to equilibrium. This may be an uncomfortable or unnatural feeling for a user, and disengaging the spring may allow the spring to return to equilibrium, thereby eliminating the spring force and resolving the discomfort. In some variations, the lower limb prosthesis may be configured such that a user may not experience an uncomfortable feeling when the spring is loaded for a prolonged period of time. For example, an actuator of the lower limb prosthesis may provide a torque in an opposite direction to the torque produced as a result of the spring force so that the user experiences an overall torque at or near zero. In order to maintain the overall torque at or near zero, the actuator may need to produce a torque for a prolonged period of time, which may result in the actuator overheating or consuming an undesired amount of energy or battery life. Thus, when a sensor of the lower limb prosthesis provides a signal to a controller indicating that the spring has been loaded for a predetermined period of time, the controller may send a signal to the engagement mechanism that results in disengagement of the spring, and the actuator may stop producing a counteracting torque.

Figure 12:
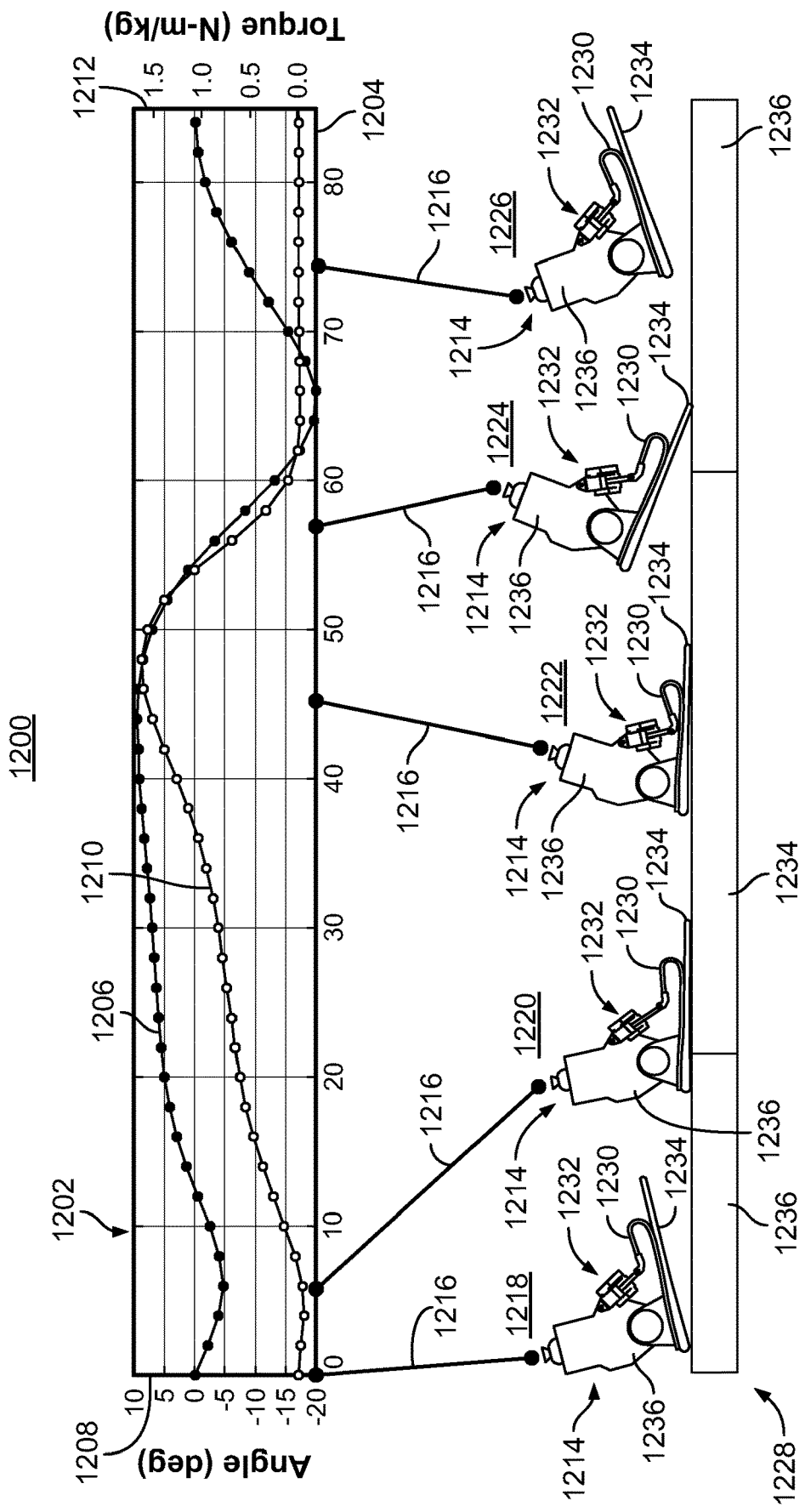
FIG. 12 is a diagram that illustrates properties of a variation of a lower limb prosthesis during different phases of the gait cycle.

In some variations, the lower limb prosthesis may be configured to engage and disengage the spring at specific times during ambulation. This may allow the spring to store energy and provide a spring force during specific phases of gait. FIG. 12 is a diagram illustrating properties of a lower limb prosthesis, including the state of a spring, during different phases of the gait cycle. Diagram 1200 includes graph 1202, which may depict properties of a variation of a lower limb prosthesis during a portion of one stride of the gait cycle on flat ground. X-axis 1204 may indicate the percentage of a stride, from heel strike at 0% to mid-swing at about 85%. Line 1206 may indicate an angle between a foot member and a main body of the lower limb prosthesis during the stride, with the angle in degrees shown on first y-axis 1208 (in some variations, 0 degrees may correspond to a 90 degree angle between the foot member and the main body). Line 1210 may indicate a torque applied about a joint axis of the lower limb prosthesis during the stride, with the magnitude shown on second y-axis 1212. It should be appreciated that the values indicated by lines 1206 and 1210 may be different for different variations of lower limb prostheses and/or for ambulation on different slopes or with different heel heights.

Diagram 1200 also shows lower limb prosthesis 1214 in various positions, and lower limb prosthesis 1214 may be similar to lower limb prosthesis 1000 described with respect to FIGS. 10A-10K. Each position depicted may correspond to the position of lower limb prosthesis 1214 during a different stage or phase of the gait cycle (stages 1218, 1220, 1222, 1224, and 1226), and lines 1216 may indicate where in the stride each of these stages may occur. Bar 1228 may indicate the portions of the stride when spring 1230 of lower limb prosthesis 1214 may be engaged with engagement mechanism 1232, indicated by section 1234, or disengaged, indicated by sections 1236.

During stage 1218, which corresponds to heel strike, spring 1230 of lower limb prosthesis 1214 may be disengaged from engagement mechanism 1232. This may allow foot member 1234 to plantarflex and contact the ground without encountering resistance from spring 1230. Stage 1220 may be the point in the gait cycle when foot member 1234 first becomes flat on the ground, which may be the point of maximum plantar flexion between heel strike and push off. At this point, spring 1230 may become engaged by engagement mechanism 1232. As will be described in detail herein, it may be advantageous for spring 1230 to be in equilibrium when it is engaged. In some variations, spring 1230 may be engaged when the angular velocity of foot member 1234 relative to main body 1236 is approximately zero.

After spring 1230 is engaged, dorsiflexion from the position shown in stage 1220 may cause spring 1230 to be loaded and store energy. Stage 1222 may correspond to the stage in the stance phase when lower limb prosthesis 1214 is maximally dorsiflexed. Thus, at this point, spring 1230 may be maximally loaded and may store the maximum amount of energy during the current stride. After stage 1222, plantar flexion may occur as lower limb prosthesis 1214 starts to push off. As foot member 1234 is plantarflexed, spring 1230 may become unloaded and provide a spring force to foot member 1234. Stage 1224 may correspond to a point during push off when spring 1230 may be disengaged. As shown, the angle between foot member 1234 and main body 1236 when spring 1230 is disengaged may be the same as it was in stage 1220 when spring 1230 was engaged. In other variations, however, the angles between foot member 1234 and main body 1236 when spring 1230 is engaged and disengaged during a stride may be different. Spring 1230 may remain disengaged after push off and throughout the swing phase when lower limb prosthesis 1214 is off of the ground, which is shown in stage 1226. Disengaging spring 1230 during the swing phase may allow foot member 1234 to be dorsiflexed for toe clearance without resistance from spring 1230.

As mentioned, configuring an engagement mechanism to engage and disengage a spring may allow the spring to store and provide energy during specific phases of the gait cycle. However, especially when a user is ambulating over terrain with different slopes, the angle between the foot member and the main body of the lower limb prosthesis may be different during the same phase of gait with different strides. For example, returning to FIG. 12, the angle between foot member 1234 and main body 1236 may be different between strides during stage 1220 when foot member 1234 first becomes flat on the ground and spring 1230 is engaged. In some variations, this may result in spring 1230 being loaded instead of in equilibrium when it is engaged during certain strides, which may, for example, provide undesired resistance to motion of foot member 1234 relative to the main body 1236 and/or cause undesired variability in the amount of energy stored or provided by spring 1230 between different strides.

In some variations, in order for a spring of a lower limb prosthesis to be in equilibrium and provide maximum energy at the most advantageous times during the gait cycle, regardless of the slope of the terrain, the engagement mechanism may be configured to adjust the engagement position of the spring. As mentioned, the engagement position may be the position where the spring directly or indirectly engages the main body. When the spring engages the main body via an engagement mechanism, the engagement position may be the position where the spring engages the engagement mechanism relative to the main body. Each engagement position of the spring may correspond to a different neutral position of the lower limb prosthesis, and thus, adjusting the engagement position may change the neutral position. The neutral position may be the position of the lower limb prosthesis when the engaged spring is in equilibrium. For example, the neutral position of the lower limb prosthesis may be an angular position of the foot member relative to the main body when the engaged spring is in equilibrium. An engagement mechanism may be configured to adjust the engagement position and corresponding neutral position for each stride during ambulation such that the spring may be in equilibrium when it is engaged after heel strike, regardless of the angle between the foot member and the main body. In some variations, the engagement mechanism may adjust the engagement position by disengaging the spring from a first engagement position and engaging it at second, different engagement position.

Figure 10F:
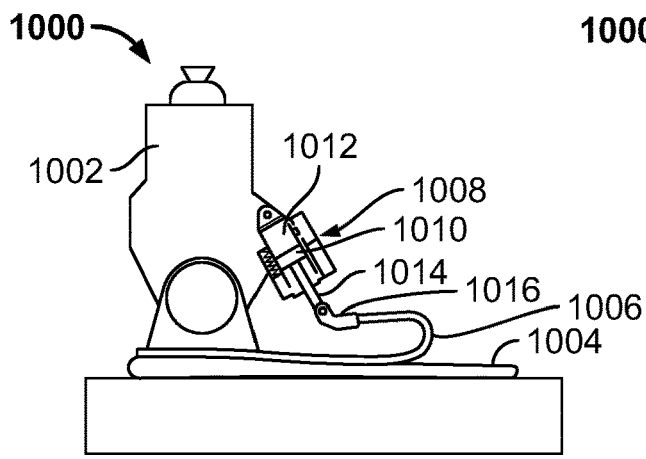
Figure 10G:
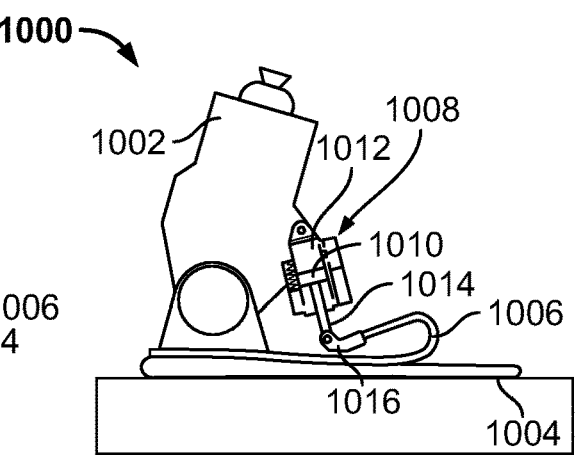
Figure 10H:
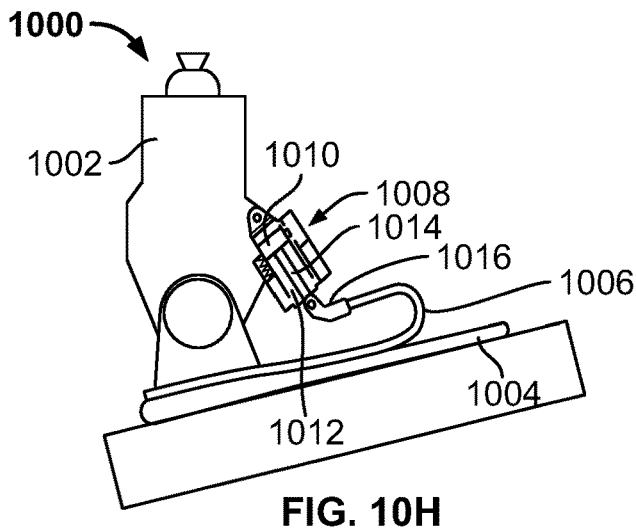
Figure 10I:
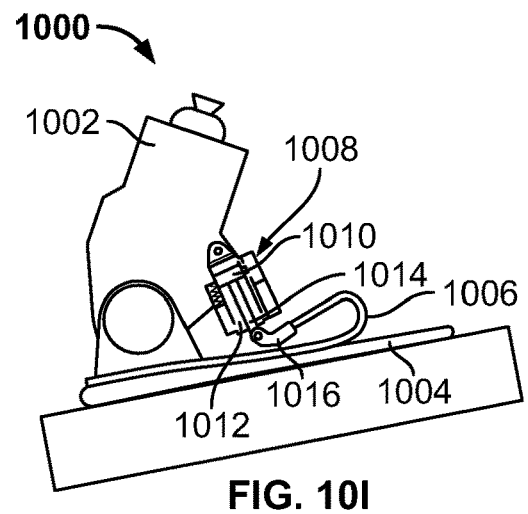
Figure 10J:
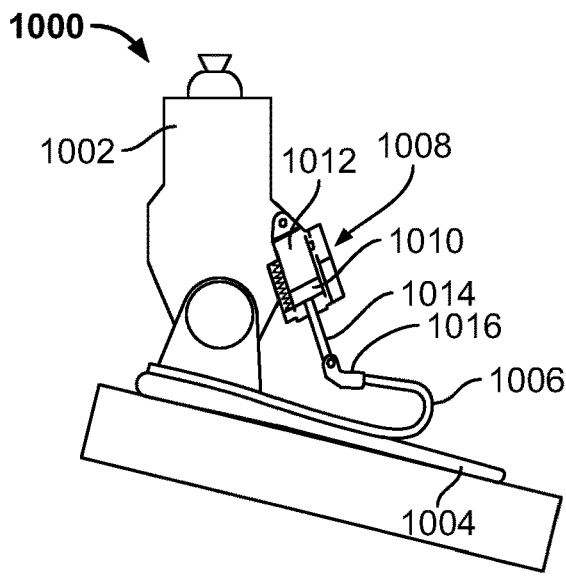
Figure 10K:
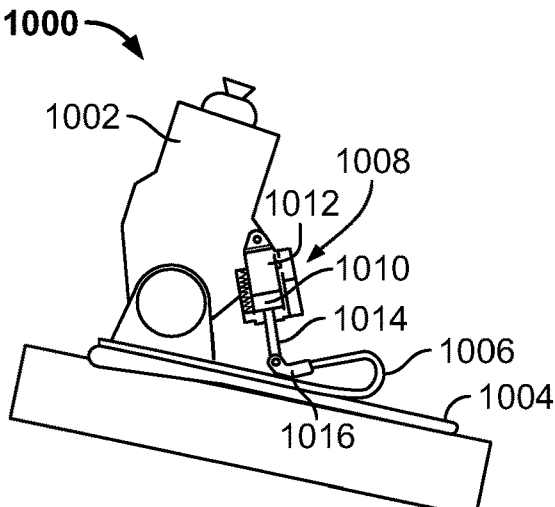

FIGS. 10F-10K are schematic representations of a variation of a lower limb prosthesis in various positions and illustrate the concept of adjusting the engagement position of a spring and thereby changing the neutral position of the lower limb prosthesis. FIGS. 10F and 10G show spring 1006 of lower limb prosthesis 1000 engaged at a first engagement position with spring 1006 in equilibrium and loaded, respectively. FIGS. 10H and 10I show spring 1006 engaged in a second engagement position with spring 1006 in equilibrium and loaded, respectively. FIGS. 10J and 10K show spring 1006 engaged in a third engagement position with spring 1006 in equilibrium and loaded, respectively. As mentioned, the engagement position may be the position where spring 1006 engages main body 1002. As spring 1006 engages main body 1002 via engagement mechanism 1008, the engagement position may be the position where spring 1006 engages engagement mechanism 1008 relative to main body 1002. For example, spring 1006 may engage engagement mechanism 1008 at contact 1016, and thus, the engagement position may be the position of contact 1016 relative to main body 1002. As mentioned, the engagement positions may be different between FIGS. 10F, 10H, and 10J, and as shown, the position of contact 1016 relative to main body 1002 is different in each of these figures. In the variation of engagement mechanism 1008 shown in FIGS. 10F-10K, spring 106 and contact 1016 may be coupled to piston 1010, which may be slidably disposed within chamber 1012. In order for engagement mechanism 1008 to change the engagement position of spring 1006, piston 1010 may slide and lock at a different positions relative to chamber 1012, thereby changing the positions of contact 1016 and spring 1006 relative to main body 1002.

Each engagement position of spring 1006 may correspond to a different neutral position of lower limb prosthesis 1000. As mentioned, the neutral position of lower limb prosthesis 1000 may be the angle between foot member 1004 and main body 1002 when the engaged spring is in equilibrium. For example, FIGS. 10F, 10H, and 10J show engaged spring 1006 in equilibrium at three different engagement positions, and thus these figures also show lower limb prosthesis 1000 in three different neutral positions. In other words, engaged spring 1006 may be in equilibrium in FIGS. 10F, 10H, and 10J, but the angle between foot member 1004 and main body 1002 may be different in each of these figures. As shown, this may allow engaged spring 1006 to be in equilibrium when foot member 1004 is on flat ground, on an incline, or on a decline, as shown in FIGS. 10F, 10H, and 10J respectively. Dorsiflexion from any of the neutral positions shown in FIGS. 10F, 10H, and 10J may result in loading of spring 1006. Thus, spring 1006 is shown loaded in FIGS. 10G, 10I, and 10K, which depict lower limb prosthesis 1000 dorsiflexed relative to the respective neutral positions shown in FIGS. 10F, 10H, and 10J.

Figure 11:
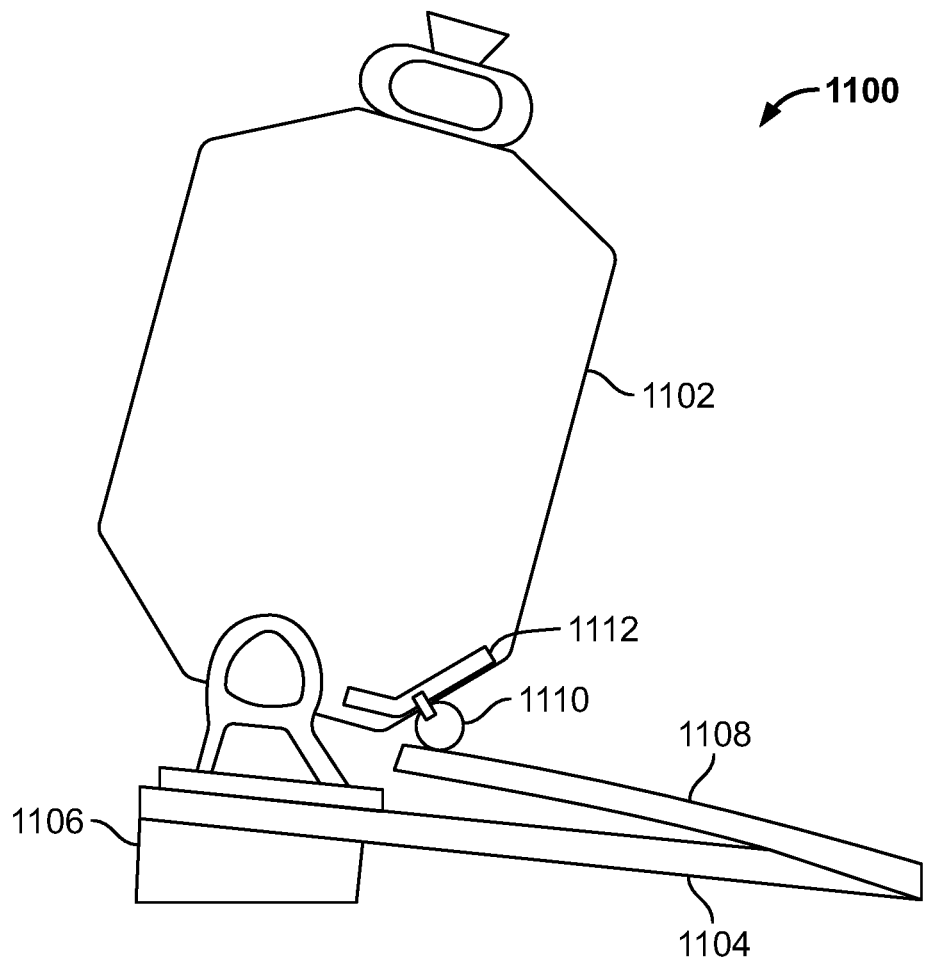
FIG. 11 is a schematic representation of a variation of a lower limb prosthesis that comprises a heel.

In addition to allowing a spring to function optimally when a lower limb prosthesis is on various slopes, adjusting the engagement position and the neutral position may also allow the spring to function optimally when different sized heels are used with the lower limb prosthesis. For example, FIG. 11 depicts a variation of a lower limb prosthesis with a heel. As shown, lower limb prosthesis 1100 may comprise main body 1102, foot member 1104, heel 1106, spring 1108, contact 1110, and engagement mechanism 1112. Heel 1106 may be coupled to or integrally formed with foot member 1104, or heel 1106 may be part of a shoe on lower limb prosthesis 1100. Adjustment of the engagement and neutral positions by engagement mechanism 1112 and contact 1110 in order to compensate for heel 1106 may be similar to the adjustment of the engagement and neutral positions of a lower limb prosthesis without a heel that is on ground with a downward slope.

Different variations of lower limb prostheses may comprise engagement mechanisms with different structures. For example, turning back to FIGS. 9A-9C, engagement mechanism 912 of lower limb prosthesis 900 may comprise a track. Contact 914 may be coupled to or integrally formed with spring 908, and it may be configured to move along the track of engagement mechanism 912 to at least temporarily couple spring 908 to engagement mechanism 912. Contact 914 may releasably lock into different engagement positions along the track of engagement mechanism 912, thereby changing the position where spring 908 engages engagement mechanism 912 and main body 902. In some variations, the engagement positions into which contact 914 may releasably lock may be at pre-set locations along the length of the track, whereas in other variations contact 914 may releasably lock at any location along the length of the track. In other variations, engagement mechanism 912 may comprise another mechanism, such as a gear mechanism, which may rotate or otherwise move contact 914 relative to main body 902 in order to change the engagement position of spring 908.

As another example, returning to FIGS. 7D and 7E, lower limb prosthesis 700 may comprise contact 711, which may be coupled to or integrally formed with spring 708, and engagement mechanism 713. Engagement mechanism 713 may move relative to main body 704, moving contact 711 relative to main body 704 accordingly, and thereby adjusting the engagement position of spring 708.

Figure 13:
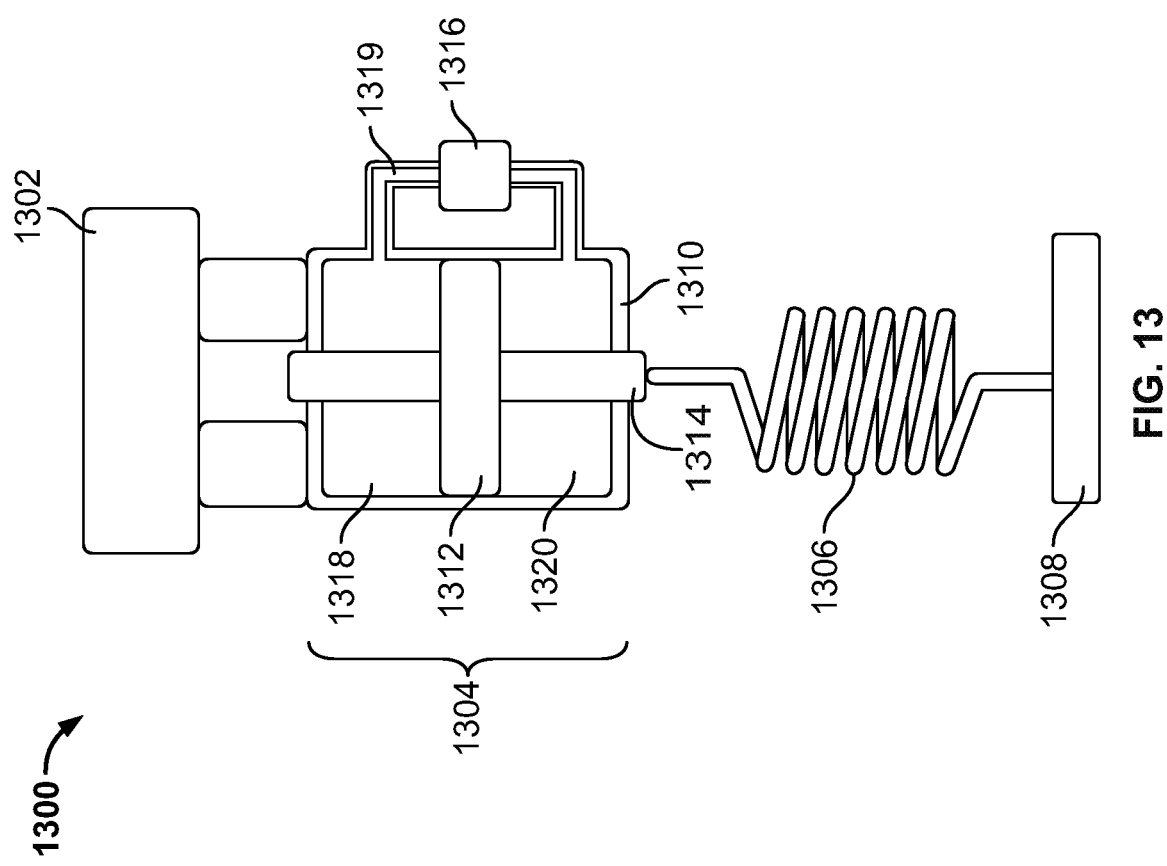
FIG. 13 is a schematic representation of a portion of a variation of a lower limb prosthesis that comprises a hydraulic engagement mechanism.

FIG. 13 is a schematic depiction of a portion of a lower limb prosthesis illustrating a variation of an engagement mechanism comprising a hydraulic system in series with a spring. As shown, lower limb prosthesis 1300 may comprise main body 1302, engagement mechanism 1304, spring 1306, and foot member 1308. Spring 1306 may be coupled to foot member 1308 and engaged with main body 1302 through engagement mechanism 1304. Engagement mechanism 1304 may comprise a hydraulic system comprising chamber 1310, piston 1312, piston rod 1314, and valve 1316. Chamber 1310 may be at least partially filled with a hydraulic fluid having zero or near zero compressibility. Piston 1312 may be slidably disposed within chamber 1310, and piston 1312 may separate chamber 1310 into first side 1318 and second side 1320. Piston 1312 may be coupled to or integrally formed with piston rod 1314, which may connect piston 1312 to spring 1306.

Valve 1316 may be fluidly connected to first side 1318 and second side 1320 via connecting passage 1319. By controlling the flow of fluid between first side 1318 and second side 1320, valve 1316 may control when spring 1306 is engaged or disengaged. For example, when valve 1316 is open, fluid may flow between first side 1318 and second side 1320, which may allow piston 1312 to slide within chamber 1310. Thus, when valve 1316 is open, spring 1306 may be disengaged. In other words, when valve 1316 is open, changes in an angle and distance between main body 1302 and foot member 1308 may result in the sliding of piston 1312 and little or no energy storage in spring 1306. When valve 1316 is closed, hydraulic fluid may not move between first side 1318 and second side 1320, and piston 1312 may remain substantially stationary relative to chamber 1310. Thus, when valve 1316 is closed, spring 1306 may be engaged, and changes in an angle and distance between main body 1302 and foot member 1308 may result in changes in the amount of energy stored in spring 1306.

Figure 14:
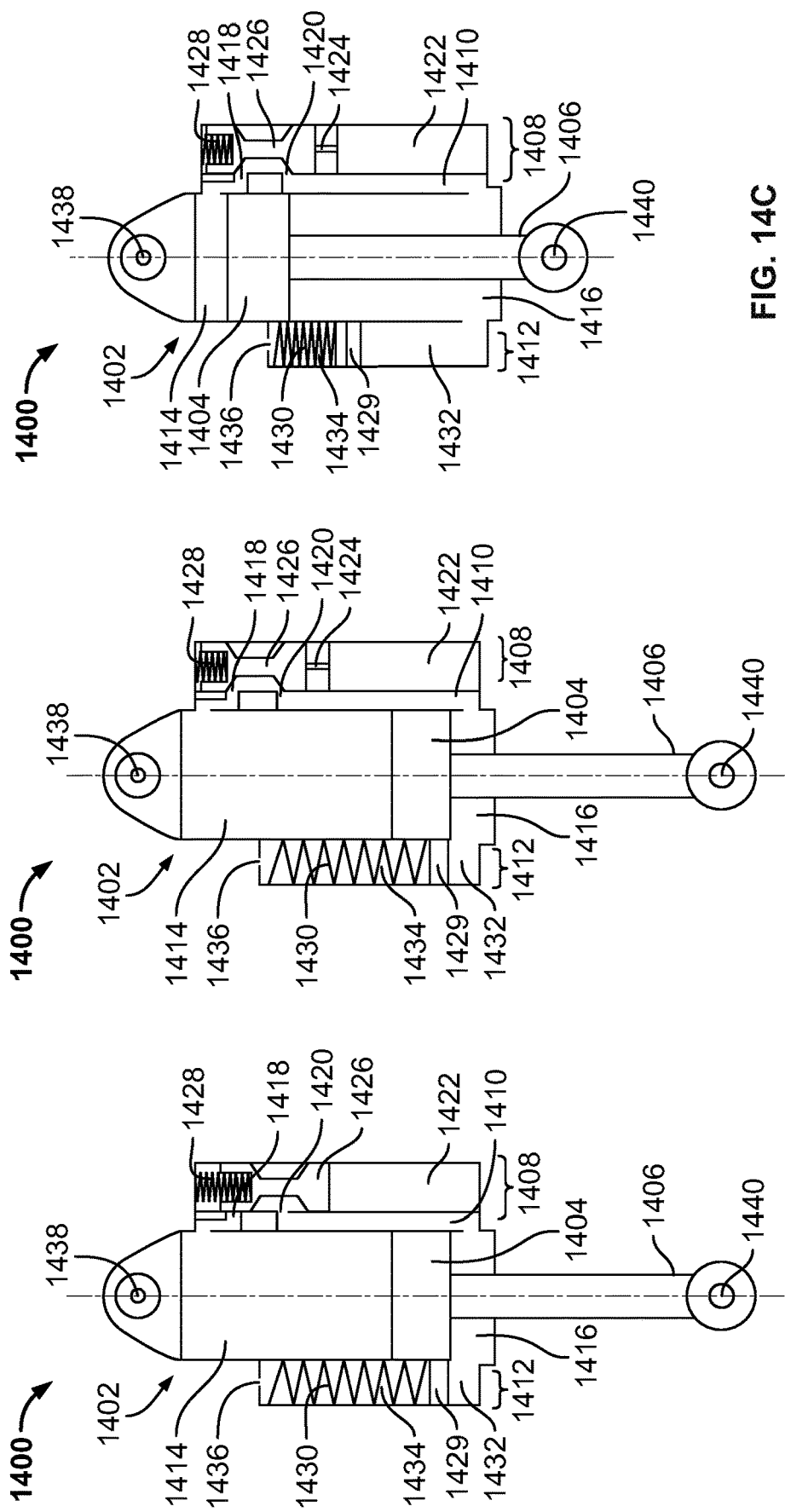
FIGS. 14A-14C are schematic representations of a variation of a hydraulic engagement mechanism in various positions.

FIGS. 14A-14C are schematic depictions of another variation of an engagement mechanism that comprises a hydraulic system. As shown, engagement mechanism 1400 may comprise a hydraulic system comprising chamber 1402, piston 1404, piston rod 1406, solenoid valve 1408, connecting passage 1410, and reservoir 1412. Piston 1404 may be slidably disposed within chamber 1402, and piston 1404 may separate chamber 1402 into first side 1414 and second side 1416. Chamber 1402 may be at least partially filled with a hydraulic fluid, and solenoid valve 1408 may be fluidly connected to first side 1414 and second side 1416 via connecting passage 1410. When solenoid valve 1408 is open, as shown in FIGS. 14B and 14C, the hydraulic fluid may flow between first side 1414 and second side 1416, and piston 1404 may slide within chamber 1402. When solenoid valve 1408 is closed, as shown in FIG. 14A, the hydraulic fluid may not move between first side 1414 and second side 1416, and piston 1404 may be substantially fixed relative to chamber 1402. Engagement mechanism 1400 may be connected in series with a spring, such that when solenoid valve 1408 is open and piston 1404 may slide within chamber 1402, the spring may be disengaged. Similarly, when solenoid valve 1408 is closed and piston 1404 is fixed, the spring may be engaged.

When solenoid valve 1408 is open, as shown in FIGS. 14B and 14C, hydraulic fluid may move between first side 1414 and second side 1416 by flowing through connecting passage 1410 and ports 1418 and 1420. As shown in FIG. 14A, when solenoid valve 1408 is closed, port 1418 may be blocked or sealed, thereby preventing hydraulic fluid from flowing between first side 1414 and second side 1416. While only port 1418 is shown blocked when solenoid valve 1408 is closed, in other variations port 1418, port 1420, and/or connecting passage 1410 may be blocked or sealed when solenoid valve 1408 is closed.

Solenoid valve 1408 may comprise solenoid 1422, plunger 1424, seal 1426, which may be coupled to plunger 1424, and return spring 1428. Solenoid 1422 may convert electrical energy to mechanical energy, which may result in linear motion of plunger 1424 and seal 1426. As shown in FIGS. 14B and 14C, when solenoid 1422 is activated by a current, plunger 1424 and seal 1426 may move away from solenoid 1422 and port 1418 may be opened (i.e., solenoid valve 1408 may be open). When solenoid 1422 is deactivated, return spring 1428 may push seal 1426 and plunger 1424 towards solenoid 1422, and seal 1426 may block or seal port 1418 (i.e., solenoid valve 1408 may be closed). In other variations, activating solenoid 1422 may close solenoid valve 1408, and deactivating solenoid 1422 may open solenoid valve 1408.

In some variations, the volume of hydraulic fluid within engagement mechanism 1400 may be constant regardless of the position of piston 1404. However, the volume of hydraulic fluid within chamber 1402 may change as piston rod 1406 is advanced into and withdrawn from chamber 1402. Reservoir 1412 may be configured to contain a variable volume of hydraulic fluid in order to compensate for the changes in hydraulic fluid volume in chamber 1402. As shown, reservoir 1412 may comprise floating piston 1429, which may be attached to reservoir spring 1430. Floating piston 1429 may separate reservoir 1412 into fluid portion 1432 and open portion 1434, and floating piston 1429 may slide within reservoir 1412 to change the volumes of fluid portion 1432 and open portion 1434. Fluid portion 1432 may be fluidly connected to chamber 1402, and it may be configured to contain hydraulic fluid. Open portion 1434 may be at least partially filled with fluid and/or gas, and the fluid and/or gas may enter and exit open portion 1434 through opening 1436 as the volume of open portion 1434 changes.

When piston rod 1406 is advanced into chamber 1402, moving from the position shown in FIG. 14B to the position shown in FIG. 14C, for example, hydraulic fluid may be displaced from chamber 1402. The hydraulic fluid displaced from chamber 1402 may enter fluid portion 1432 of reservoir 1412, thereby increasing the volume of hydraulic fluid in fluid portion 1432. As the volume of hydraulic fluid in fluid portion 1432 increases, floating piston 1429 may be displaced towards open portion 1434, and the volume of open portion 1434 may decrease. When piston rod 1406 is withdrawn from chamber 1402, hydraulic fluid may be pulled from fluid portion 1432 into chamber 1402, thereby decreasing the volume of hydraulic fluid in fluid portion 1432. As the volume of hydraulic fluid in fluid portion 1432 decreases, floating piston 1429 may be displaced towards fluid portion 1432, which may be aided by reservoir spring 1430, and the volume of open portion 1434 may increase.

Engagement mechanism 1400 may be coupled to a main body via connector 1438 and coupled to a spring via contact 1440. In other variations, engagement mechanism 1400 may be coupled to the spring via connector 1438 and the main body via contact 1440. Connector 1438 and/or contact 1440 may each comprise a joint that allows at least some rotation of engagement mechanism 1400 relative to the main body and/or the spring. For example, connector 1438 and/or contact 1440 may each comprise a pin joint, a ball or spherical joint, or the like. Coupling engagement mechanism 1400 to the main body and/or the spring with an element that allows rotation may eliminate or decrease any bending moment that may be applied to engagement mechanism 1400. This may be advantageous as a bending moment may result in damage and/or compromised function of engagement mechanism 1400.

Figure 15:
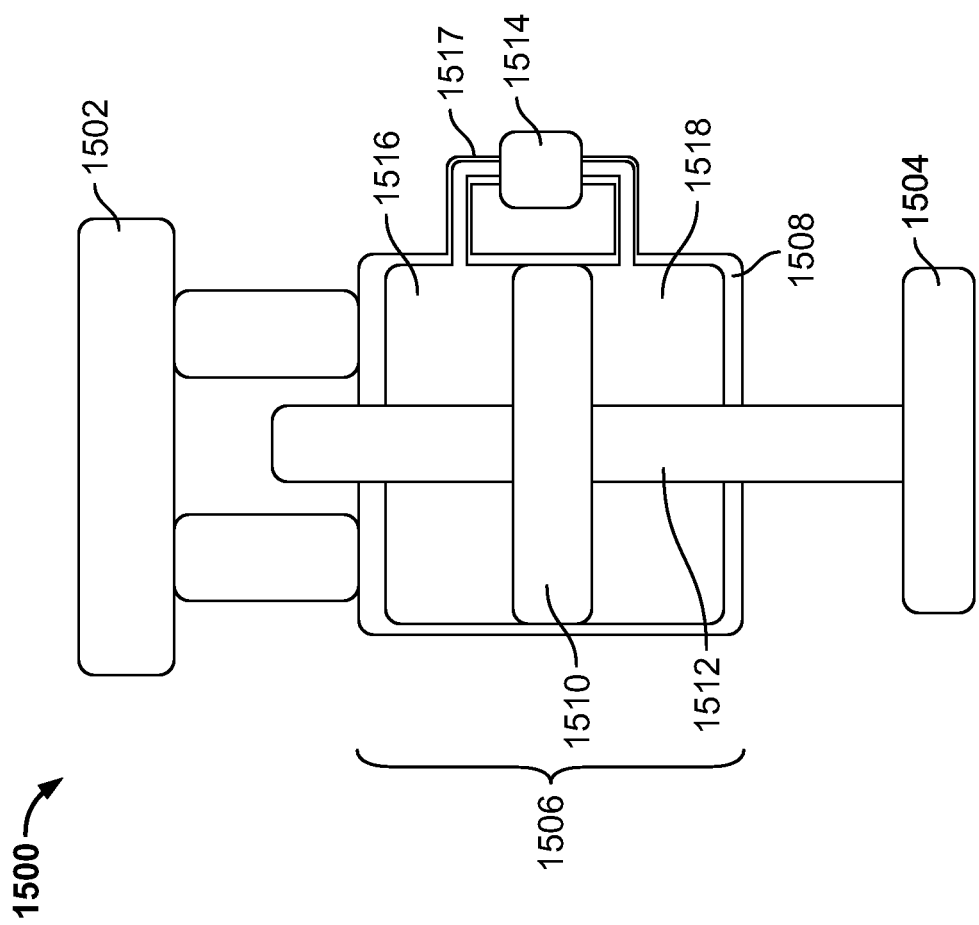
FIG. 15 is a schematic representation of a portion of a variation of a lower limb prosthesis that comprises a combined spring and engagement mechanism.

In some embodiments, the lower limb prostheses described here may comprise an engagement mechanism that is integrated or otherwise combined with the spring. For example, FIG. 15 is a schematic depiction of a variation of a portion of a lower limb prosthesis comprising a combined spring and engagement mechanism. As shown, lower limb prosthesis 1500 may comprise main body 1502, foot member 1504, and combined spring and engagement mechanism 1506, which may be coupled to main body 1502 and foot member 1504. Combined spring and engagement mechanism 1506 may comprise chamber 1508, which may be at least partially filled with a compressed gas, piston 1510, piston rod 1512, and valve 1514. Piston 1510 may be slidably disposed within chamber 1508, and it may separate chamber 1508 into first side 1516 and second side 1518. As shown, piston rod 1512, which may be integrally formed with or coupled to piston 1510, may connect piston 1510 to foot member 1504. Alternatively, in other variations piston rod 1512 may connect piston 1510 to main body 1502.

Valve 1514 may be fluidly connected to first side 1516 and second side 1518 via connecting passage 1517. By controlling flow between first side 1516 and second side 1518, valve 1514 may control engagement and disengagement of combined spring and engagement mechanism 1506. When valve 1514 is closed, compressed air may not flow between first side 1516 and second side 1518, and combined spring and engagement mechanism 1506 may be in an engaged state. When combined spring and engagement mechanism 1506 is in the engaged state, combined spring and engagement mechanism 1506 may function as an air or gas spring. In other words, changes in an angle and distance between main body 1502 and foot member 1504 may result in further compression of gas on first side 1516 or second side 1518, thereby storing energy by creating a pressure differential between first side 1516 and second side 1518. When combined spring and engagement mechanism 1506 is engaged, it may be configured to apply a spring force to foot member 1504 and main body 1502. When valve 1514 is open, compressed air may flow between first side 1516 and second side 1518, and piston 1510 may slide within chamber 1508 without creating a substantial pressure differential. Thus, when valve 1514 is open, combined spring and engagement mechanism 1506 may be disengaged, and changes in an angle and distance between main body 1502 and foot member 1504 may not result in changes in the amount of energy stored in combined spring and engagement mechanism 1506.

In some variations, an engagement mechanism may be in electronic communication with a controller, and the engagement mechanism may be controlled by receiving one or more commands from the controller. The one or more commands may control the engagement mechanism to engage a spring, disengage the spring, or adjust an engagement position of the spring. The control of the engagement mechanism may be based at least partially on signals received by the controller from one or more sensors. For example, returning to FIGS. 9A-9C, the control of engagement mechanism 912 may be at least partially based on an engagement position signal provided by engagement position sensor 924. The engagement position signal may indicate the engagement position of spring 908. In some variations, the engagement position of spring 908 may be determined by detecting a position of contact 914 relative to engagement mechanism 912. In other variations, the engagement position of spring 908 may be determined by detecting a position of a portion of spring 908 (e.g., a proximal portion) or a portion of engagement mechanism 912. Engagement position sensor 924 may comprise any suitable position sensor, such as a Hall effect sensor, an optical sensor, a contact sensor, an inductive sensor, or the like.

In some variations, an engagement mechanism of a lower limb prosthesis may be at least partially controlled based one or more signals provided by one or more sensors other than an engagement position sensor. For example, an engagement mechanism may be at least partially controlled based on a torque and/or force signal provided by a torque and/or force sensor to a controller. A torque and/or force signal may indicate, for example, a torque and/or force applied to a foot member. In some variations, the controller may use this information to control the engagement mechanism, for example, by causing the engagement mechanism to disengage the spring if a torque and/or force applied to the foot member is sustained for longer than a predetermined time.

In some variations, an engagement mechanism may be controlled based on information provided to a controller by an IMU, an absolute encoder, and/or one or more other sensors that indicates an orientation or position of a foot member. For example, an IMU may provide an orientation signal that indicates a pitch of the foot member (e.g., an amount of dorsiflexion or plantar flexion, an angle between the foot member and the main body). Additionally or alternatively, an absolute encoder may provide a position signal that indicates an angular position of the foot member relative to the main body. The controller may use the orientation and/or position signals to determine, for example, a phase of gait, a slope of the ground, and/or a heel height of the lower limb prosthesis. The controller may use this information to control the engagement mechanism to engage, disengage, or adjust an engagement position of the spring to allow the spring to store and provide energy at the most advantageous times during the gait cycle, regardless of the slope of the ground or the height of a heel.

Joint

A lower limb prosthesis may comprise a joint, which may be the portion of the lower limb prosthesis that couples a main body to a foot member. In addition, the joint may facilitate rotation of the main body and the foot member relative to one another. The joint may comprise a portion of the main body or an element coupled to the main body, and a portion of the foot member or an element coupled to the foot member. In some variations, the joint may comprise a shaft that is coupled to a hub. The shaft may be, for example, an output shaft of a transmission or a shaft that is coupled to or integrally formed with the output shaft of the transmission. The hub may comprise an opening and may be, for example, a portion of the foot member or a foot coupler that is attached to or integrally formed with the foot member. The shaft may be positioned at least partially within the opening of the hub, and the size and shape of the shaft may correspond to the size and shape of the hub opening so that the shaft tightly fits within the hub opening. The shaft may transmit a torque, such as an output torque of the transmission, to the hub such that rotation of the shaft may result in rotation of the hub, thereby causing the main body and the foot member to rotate relative to one another.

The shaft of the joint may transmit a torque to the hub in one or more ways. For example, the shaft and hub opening may comprise one or more mating splines. The splines may be involute, parallel, crowned, helical, serrated, or the like. In some variations, torque may be transmitted via one or more keys, pins, or the like on the shaft and/or the hub. The shaft and the opening of the hub may have any suitable cross-sectional shape. For example, returning to FIG. 1, joint 104 may comprise output shaft 116 of the transmission and foot coupler 106, and output shaft 116 may be at least partially inserted into opening 117 of foot coupler 106. As shown, the cross-sectional shape of output shaft 116 and of opening 117 may be circular. In other variations, such as in joint 306 shown in FIG. 3, output shaft 346 and opening 347 of foot coupler 308 may each have a polygonal cross-sectional shape. While the polygonal cross-sectional shape in FIG. 3 is triangular, a shaft and a hub opening may have any suitable cross-sectional shape (e.g., rectangular, pentagonal, hexagonal, or a shape with more than 6 sides). In some variations, a shaft and a hub opening of a joint may have an irregular cross-sectional shape.

In variations where the hub of the joint is a foot coupler, the foot coupler may be attached to the foot member in any suitable way. For example, the foot coupler may be attached to the foot member with one or more fasteners such as screws, bolts, or the like and/or an adhesive. In some variations, the foot coupler may comprise one or more structural beams, which may, for example, support one or more sensors. The foot coupler may be made of the same or different materials as the foot member and/or the main body.

Foot Member

A lower limb prosthesis may comprise a foot member which may interact with the ground. The foot member may apply a torque transmitted by a transmission to the ground in order, for example, to propel a user during gait. The lower limb prosthesis may be modular such that any foot member may be coupled to a main body. The foot member may be coupled directly to the main body or indirectly, such as via a foot coupler. In some variations, the foot member may comprise carbon fiber, which may be arranged in multiple layers, fiberglass, or any other suitable materials.

Methods of Use

A lower limb prosthesis may be used to perform at least some of the functions of a natural lower limb, such as facilitating energy efficient ambulation. A method of ambulating may comprise the lower limb prosthesis determining the phase or stage of gait (e.g., stance, swing, heel strike, push off), controlling the torque output of an actuator, and/or controlling the operation of a spring that acts in parallel to the torque produced by the actuator. In some variations, the method of ambulating may comprise a controller responding to information provided by one or more sensors. For example, one or more sensors may provide a signal to the controller indicating information about the current state of the lower limb prosthesis, and the controller may deliver a command based on this signal to the actuator and/or an engagement mechanism.

Initial Setup

In some variations, a method of use of a lower limb prosthesis may comprise an initial setup, which may allow one or more operational parameters of the lower limb prosthesis to be set for a specific user via a user interface. The method of initial setup may comprise setting one or more timing levels and/or one or more strength levels for different walking speeds, such as a slow, normal, and/or fast walking speed. In some variations, the timing level may be a condition or a parameter that triggers certain operations of the lower limb prosthesis to start, stop, or change. The timing level may be a specific value or threshold (e.g., one specific angle, one specific torque), or it may have a range or a sensitivity (e.g., a range of angles, a range of torques). The strength level may determine the magnitude of an action or an operation performed by the lower limb prosthesis. For example, the strength level may determine the magnitude of a torque produced by an actuator at a specific time (e.g., during a specific phase of gait, when a certain timing level has been reached).

In some variations, the timing level may be a parameter that triggers the start of a push-off stage of gait. For example, the timing level may be a certain angle between a foot member and a main body (e.g., an absolute angle, an angle relative to a neutral position). When this angle is reached, a controller of the lower limb prosthesis may start one or more operations that occur during push off. For example, when the timing level is reached, the controller may provide a torque command to an actuator to cause the actuator to produce a torque that may result in plantar flexion. The magnitude of the torque produced may be determined, at least in part, by a strength level that may be set during initial setup. In some variations, different timing levels may be associated with different strength levels. For example, different magnitudes of torques may be produced when different angles between the foot member and the main body are reached.

While the adjustment of operational parameters may be performed during an initial setup, it should be appreciated that one or more of the same or different operational parameters may be adjusted after the initial setup. A user interface that may be used to adjust one or more operational parameters for initial setup and/or later adjustment may be wired to the lower limb prosthesis or it may communicate wirelessly with the lower limb prosthesis (e.g., using Bluetooth, infrared, wireless fidelity (Wi-Fi), or the like). In some variations, it may be advantageous for the user interface to communicate wirelessly with the lower limb prosthesis, as this may allow one or more operational parameters to be adjusted remotely.

Ambulation

During ambulation, the controller of the lower limb prosthesis may determine what phase or stage of gait the lower limb prosthesis is in. The controller may determine the phase of gait based on one or more signals provided by one or more sensors. In some variations, a torque and/or force signal provided by a torque and/or force sensor may be used by the controller to determine the phase of gait. For example, a force sensor (e.g., a load cell) may provide a force signal indicating that a certain force is being applied to a foot member and/or a foot coupler, and the controller may use this force signal to determine that the lower limb prosthesis is weighted and in stance phase. A controller may additionally or alternatively determine the phase of gait based on other signals, including but not limited to signals that indicate a current (e.g., a current of an actuator) and/or an angular position of the foot member relative to a main body.

It may be advantageous for the controller to determine the phase of gait because the operation of the lower limb prosthesis (e.g., the commands provided by the controller, the output of the actuator, the operation of the engagement mechanism) may be different during different phases. For example, during the stance phase, the controller may provide a specific torque command to the actuator so that the actuator produces an actuator torque that results in a specific final torque being applied to the foot member by a transmission. The controller may determine what torque command to provide based on a control algorithm, such as a control algorithm stored in memory of the controller, and/or prosthetic information provided by one or more sensors.

In some variations, the controller may determine what torque command to provide during the push-off phase of gait based on a speed of ambulation and prosthetic information provided by one or more sensors during a portion of the current stance phase (i.e., the portion of the current stance phase between heel strike and when the foot member is flat on the ground). In some variations, the torque command provided by the controller may be adjusted such that a desired overall torque is applied to the foot member. The overall torque may be the sum of the torque produced by the actuator and transmitted by the transmission, and the torque produced as a result of a spring force. For example, the controller may receive a torque signal from a torque sensor positioned in proximity to the joint axis, such as on a foot coupler, which may indicate the overall torque. The controller may then adjust the torque command to adjust the torque produced by the actuator accordingly.

After push-off, when the lower limb prosthesis enters the swing phase, the controller may provide a torque command to the actuator that may result in a torque being produced in an opposite direction to the torque produced during push off. The torque command provided by the controller during the swing phase may result in dorsiflexion of the foot member from its position at the end of stance phase. This dorsiflexion of the foot member may allow the toe or distal portion of the foot member to clear the ground during the swing phase. In some variations, the torque command provided by the controller during the swing phase may result in dorsiflexion of the foot member to a position where the foot member is approximately perpendicular to the main body.

Figure 16:
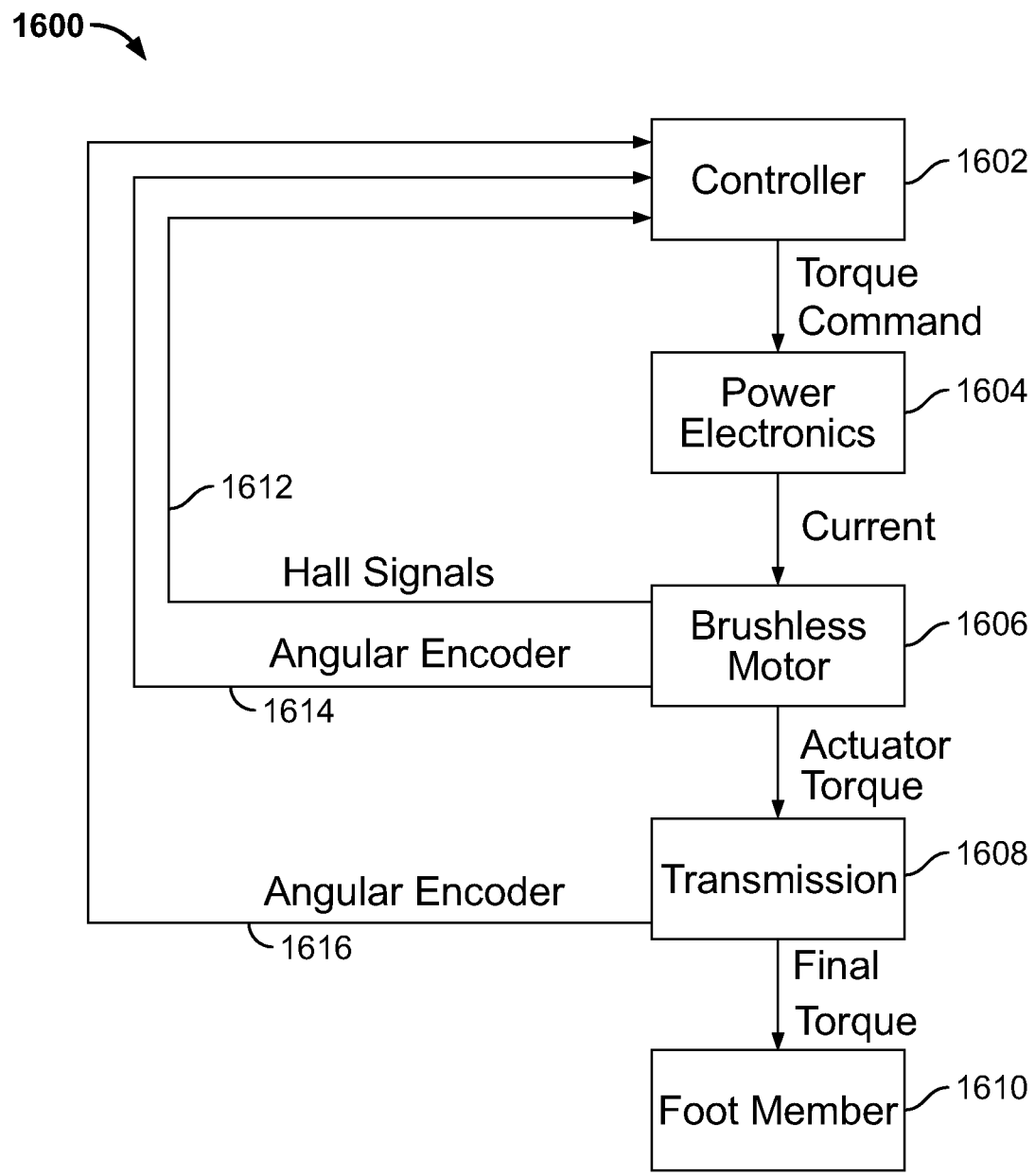
FIG. 16 is a diagram illustrating a variation of a method of controlling a torque of a lower limb prosthesis.

FIG. 16 is a diagram illustrating a variation of a method of applying a torque to a foot member of a lower limb prosthesis. As shown, method 1600 may comprise controller 1602 generating and delivering a torque command to power electronics 1604. Power electronics 1604 may convert the torque command to a current, which may be delivered to brushless motor 1606 or another actuator. In response to the current, brushless motor 1606 may apply an actuator torque to transmission 1608. Transmission 1608 may amplify the actuator torque and apply a final torque to foot member 1610. The final torque may result in dorsiflexion or plantar flexion of foot member 1610.

Controller 1602 may determine the specific torque command to generate, and thus, the final torque that is applied to foot member 1610 based on a control algorithm and feedback signals from one or more sensors. For example, signal 1612 may be a position signal provided by a Hall effect sensor that may indicate a position of a rotor of brushless motor 1606 relative to a stator of brushless motor 1606. Signal 1614 may a position signal and/or an incremental signal provided by an absolute encoder and/or an incremental encoder, respectively. Signal 1614 may indicate a position and/or an angular velocity of the rotor of brushless motor 1606. Signal 1616 may be may also be a position signal and/or an incremental signal provided by an absolute encoder and/or an incremental encoder, respectively. However, signal 1616 may indicate a position and/or an angular velocity of an output of transmission 1608, such as an output shaft, which may also indicate a position and/or an angular velocity of foot member 1610.

A method for controlling a lower limb prosthesis may comprise the use of damping during the stance phase and/or the swing phase of gait. For example, after heel strike in stance phase, damping may be provided to resist the plantar flexion motion that causes the foot member to become flat on the ground. While plantar flexion may still occur, damping may prevent the foot member from undesirably slapping the ground. Damping may additionally or alternatively be provided during the push-off stage of the stance phase. As mentioned, a controller may generate a torque command for push-off based on a torque signal provided by a torque sensor. The controller may use damping as a part of a Proportional Derivative (PD) control of the torque, and this may result in a smoother motion of the foot member during push-off.

In some variations, damping may be provided during the swing phase of gait. For example, damping may be provided through PD control in order to control the dorsiflexion motion of the foot member to achieve toe clearance and to maintain the foot member in a desired position during swing phase. In some variations, in contrast to the damping during push-off, the damping during the swing phase may be based on a measured angle, such as the angle between the foot member and the main body, and not a measured torque. Damping may also be used to brake the actuator in the event of a power failure, such as by shorting leads.

Relaxed State

In some variations, a lower limb prosthesis may be configured to enter a relaxed state when a controller determines that a user is in a relaxed position, such as sitting, lying, or any other position that does not require a torque to be applied to a foot member. For example, a position signal from an absolute encoder, an incremental signal from an incremental encoder, a torque and/or force signal from a torque and/or force sensor, and/or a velocity, acceleration or orientation signal from an IMU may be used by the controller to determine if the user is in a relaxed position. If the controller determines that the user is in a relaxed position, the controller may allow the foot member to plantarflex, such as by disengaging a spring or adjusting damping of the actuator. Additionally or alternatively, when the lower limb is in the relaxed state, the lower limb prosthesis may enter a low power state and consume less energy. If one or more of the above-referenced signals from one or more sensors exceeds a certain threshold, the controller may move the lower limb prosthesis out of the relaxed state.

Locking

In some variations, a lower limb prosthesis may comprise a lock that may be operated by a user to move the lower limb prosthesis into a locked state. In the locked state, an angle between a foot member and a main body of the lower limb prosthesis may be fixed. The lock may comprise a button, a mechanical lever, or any other suitable mechanism that locks the transmission when actuated. It may be advantageous for a lower limb prosthesis to comprise a lock, as this may serve as a safety mechanism in various situations, such as if a power loss occurs in the lower limb prosthesis or if a user is driving.

The foregoing description of the disclosed example embodiments is provided to enable any person of ordinary skill in the art to make or use the embodiments in the present disclosure. Various modifications to these examples will be readily apparent to those of ordinary skill in the art, and the principles disclosed herein may be applied to other examples without departing from the spirit or scope of the present disclosure. The described embodiments are to be considered in all respects only as illustrative and not restrictive.

What is claimed is:

1. A lower limb prosthesis, comprising:
   a foot member;
   a main body rotatably coupled to the foot member at a joint comprising a joint axis, wherein the main body comprises a housing, an actuator, and a transmission, and wherein the actuator is configured to transmit an actuator torque to the transmission, and the transmission is configured to transmit a final torque to the foot member;
   a spring coupled to the foot member and the main body, wherein the spring is configured to apply a spring force to the foot member, and wherein the spring force acts in parallel to the final torque; and
   an engagement mechanism configured to engage and disengage the spring, wherein when the spring is engaged, the spring is configured to apply the spring force to the foot member, and when the spring is disengaged, the spring is not configured to apply the spring force to the foot member.

2. The lower limb prosthesis of claim 1, wherein when the spring is engaged, the spring engages the main body at an engagement position.

3. The lower limb prosthesis of claim 2, wherein the engagement mechanism is further configured to adjust the engagement position.

4. The lower limb prosthesis of claim 3, wherein adjusting the engagement position changes a neutral position of the lower limb prosthesis, and wherein the neutral position of the lower limb prosthesis is an angular position of the foot member relative to the main body at which the engaged spring is in equilibrium.

5. The lower limb prosthesis of claim 3, further comprising a controller in electronic communication with the engagement mechanism, wherein the engagement mechanism is configured to engage the spring, disengage the spring, and adjust the engagement position in response to a signal from the controller.

6. The lower limb prosthesis of claim 5, further comprising an engagement position sensor configured to provide an engagement position signal to the controller indicating the engagement position of the spring.

7. The lower limb prosthesis of claim 5, further comprising a torque sensor configured to provide a torque signal to the controller, wherein the controller is configured to control the engagement mechanism in response to the torque signal.

8. The lower limb prosthesis of claim 5, further comprising an absolute encoder configured to provide a position signal to the controller indicating the position of the foot member relative to the main body, and wherein the controller is configured to control the engagement mechanism in response to the position signal.

9. The lower limb prosthesis of claim 3, wherein the engagement mechanism comprises a track, and wherein a portion of the spring is configured to slide along the track and reversibly lock into an engagement position on the track.

10. The lower limb prosthesis of claim 3, wherein the engagement mechanism comprises:
    a chamber at least partially filled with a hydraulic fluid;
    a piston within the chamber, wherein the piston separates the chamber into a first side and a second side;
    a piston rod connecting the piston to the spring; and
    a valve fluidly connected to the first side and the second side, wherein the valve is configured to be opened to allow hydraulic fluid to move between the first side and the second side and closed to block hydraulic fluid from moving between the first side and the second side, and wherein the piston is slidable within the chamber when the valve is open and fixed relative to the chamber when the valve is closed.

11. The lower limb prosthesis of claim 10, wherein the spring is in the engaged state when the valve is closed, and the spring is in the disengaged state when the valve is open.

12. The lower limb prosthesis of claim 11, wherein the valve is a solenoid valve.

13. The lower limb prosthesis of claim 12, further comprising a reservoir configured to contain a variable volume of hydraulic fluid in order to compensate for changes in a volume of hydraulic fluid in the chamber.

* * * * *